(12) United States Patent
Huang et al.

(10) Patent No.: US 11,801,310 B2
(45) Date of Patent: Oct. 31, 2023

(54) COMPOSITION FOR IMPROVING THE SOLUBILITY OF POORLY SOLUBLE SUBSTANCES, USE THEREOF AND COMPLEX FORMULATION CONTAINING THEREOF

(71) Applicant: Industrial Technology Research Institute, Hsinchu (TW)

(72) Inventors: Wen-Chia Huang, Taichung (TW); Yen-Jen Wang, Taichung (TW); Felice Cheng, Zhubei (TW); Chia-Ching Chen, Taichung (TW); Shao-Chan Yin, Tainan (TW); Chien-Lin Pan, Hsinchu (TW); Tsan-Lin Hu, Jhubei (TW); Meng-Nan Lin, Zhubei (TW); Kuo-Kuei Huang, Zhubei (TW); Maggie Lu, Zhudong Township (TW); Chih-Peng Liu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/232,601

(22) Filed: Dec. 26, 2018

(65) Prior Publication Data
US 2019/0209706 A1 Jul. 11, 2019

Related U.S. Application Data

(60) Provisional application No. 62/610,509, filed on Dec. 26, 2017.

(30) Foreign Application Priority Data

Dec. 21, 2018 (EP) ..................................... 18215590

(51) Int. Cl.
| | |
|---|---|
| *A61K 47/69* | (2017.01) |
| *A61K 47/38* | (2006.01) |
| *A61K 47/40* | (2006.01) |
| *A61K 31/4439* | (2006.01) |
| *A61K 31/569* | (2006.01) |
| *A61K 9/00* | (2006.01) |
| *A61K 47/65* | (2017.01) |
| *A61K 9/08* | (2006.01) |

(52) U.S. Cl.
CPC ........ *A61K 47/6951* (2017.08); *A61K 9/0019* (2013.01); *A61K 9/0048* (2013.01); *A61K 9/0053* (2013.01); *A61K 9/08* (2013.01); *A61K 31/4439* (2013.01); *A61K 31/569* (2013.01); *A61K 47/38* (2013.01); *A61K 47/40* (2013.01); *A61K 47/65* (2017.08)

(58) Field of Classification Search
CPC .......... A61K 9/0048; A61K 31/56–575; A61K 31/52; A61K 31/522; A61K 31/724; A61K 47/38–40; A61K 47/6951; A61K 49/189
See application file for complete search history.

(56) References Cited

U.S. PATENT DOCUMENTS

| | | | | |
|---|---|---|---|---|
| 4,559,343 | A * | 12/1985 | Han .......................... | A61P 29/00 514/263.31 |
| 4,728,509 | A * | 3/1988 | Shimizu ................... | A61P 27/02 514/291 |
| 4,994,273 | A | 2/1991 | Zentner et al. | |
| 5,494,901 | A * | 2/1996 | Javitt .................... | A61K 31/425 514/363 |
| 6,407,079 | B1 | 6/2002 | Müller et al. | |
| 7,141,540 | B2 | 11/2006 | Wang et al. | |
| 7,863,245 | B2 | 1/2011 | Quay | |
| 7,893,040 | B2 | 2/2011 | Loftsson et al. | |
| 8,329,435 | B2 | 12/2012 | Skinner | |
| 8,426,368 | B2 | 4/2013 | Haley et al. | |
| 9,358,215 | B2 | 6/2016 | Dewitt | |
| 9,492,451 | B2 | 11/2016 | Rustomjee et al. | |
| 9,597,406 | B2 | 3/2017 | Chen et al. | |
| 2003/0031715 | A1* | 2/2003 | Park ........................ | A61K 9/146 424/486 |
| 2005/0215520 | A1 | 9/2005 | Liu et al. | |
| 2006/0025380 | A1 | 2/2006 | Thorsteinsson et al. | |
| 2007/0020336 | A1* | 1/2007 | Loftsson ................ | A61K 31/42 424/486 |
| 2011/0028431 | A1 | 2/2011 | Zerbe et al. | |
| 2014/0276482 | A1 | 9/2014 | Astatieva et al. | |

(Continued)

FOREIGN PATENT DOCUMENTS

| | | |
|---|---|---|
| EP | 0213514 A2 | 3/1987 |
| EP | 0621036 A1 | 10/1994 |
| JP | 62-123116 A | 6/1987 |

(Continued)

OTHER PUBLICATIONS

Ryzhakov, A. et al "Self-assembly of cyclodextrins . . . "J. Pharm. Sci., vol. 105, pp. 2556-2569. (Year: 2016).*
Couto, A. et al "Characterisation of DM-beta-cyclodextrin:prednisolone complexes . . . " J. Incl. Phenom. Macrocycl. Chem., vol. 80, pp. 155-164. (Year: 2014).*
Popielec, A. et al "Effects of cyclodextrins of the chemical stability of drugs" Int. J. Pharm., vol. 531, pp. 532-542. (Year: 2017).*
Mura, P. et al "The influence of polyvinylpyrrolidone on naproxen complexation . . . " Eur. J. Pharm. Sci., vol. 13, pp. 187-194. (Year: 2001).*

(Continued)

*Primary Examiner* — Leigh C Maier
(74) *Attorney, Agent, or Firm* — Birch, Stewart, Kolasch & Birch, LLP

(57) ABSTRACT

A composition for improving the solubility of poorly soluble substances is provided. The composition includes about 40-99.5% by weight of cyclodextrin and/or derivatives thereof; about 0.05-10% by weight of at least one water-soluble polymer; and about 0.05-60% by weight of at least one water-soluble stabilizer.

5 Claims, 12 Drawing Sheets

(8 of 12 Drawing Sheet(s) Filed in Color)

(56) References Cited

U.S. PATENT DOCUMENTS

2016/0375150 A1  12/2016  Wu

FOREIGN PATENT DOCUMENTS

| | | |
|---|---|---|
| JP | 1-290629 A | 11/1989 |
| JP | 2002-226363 A | 8/2002 |
| JP | 2002-532565 A | 10/2002 |
| JP | 2017-524034 A | 8/2017 |
| TW | 256831 A | 9/1995 |
| TW | I568453 B | 2/2017 |
| WO | WO 2006/137433 A1 | 12/2006 |
| WO | WO 2012/110971 A2 | 8/2012 |
| WO | WO 2016/022750 A1 | 2/2016 |

OTHER PUBLICATIONS

Jug, M. et al. "Multicomponent complexes of piroxicam with cyclodextrins . . . " Drug Dev. Ind. Pharm., vol. 30, No. 10, pp. 1051-1060. (Year: 2004).*

Soliman, O. et al "Potential use of cyclodextrin complexes for enhanced stability . . . " AAPS PharmSciTech, vol. 18, No. 4, pp. 1228-1241. (Year: 2017).*

Extended European Search Report dated Jul. 2, 2019, for European Patent Application No. 18215590.3.

Santos, C., et al., "Drug delivery systems: Study of inclusion complex formation for ternary caffeine-β-cyclodextrin-water mixtures from apparent molar volume values at 298.15 K and 310.15 K," Journal of Molecular Liquids, Nov. 2016, vol. 223, pp. 209-216.

Pandya et al., "Formulation and characterization of ternary complex of poorly soluble duloxetine hydrochloride", Journal of Applied Pharmaceutical Science, 2015, vol. 5, No. 6, pp. 088-096.

"Cefditoren Pivoxil Fine Granule 10% Pediatric," Nichi-iko, Sep. 2020, pp. 1-3 (5 pages total), with English translation.

"Cefteram pivoxil," The Japanese Journal of Antibiotics, vol. XL-10, Oct. 1987, pp. 1724-1740 (18 pages total), with partial English translation.

"General Test Procedure," The Japanese Pharmacopoeia, 14th Edition, 2001, 5 pages total, with partial English translation.

Fujifilm, "Tomiron," Data Sheet, Sep. 2020, pp. 1-4 (6 pages total), with partial English translation.

Japanese Office Action for Japanese Application No. 2018-242984, dated Jan. 13, 2021, with English translation.

Huang, W.C., et al., "A corneal-penetrating eye drop formulation for enhanced therapeutic efficacy of soft corticosteroids against anterior uveitis", Journal of Drug Delivery Science and Technology 2019. pp. 1-8.

Li, R., et al., "Effect of HPMC and PVP on Inclusion of Clonazepam with Hydroxypropyl-β-cyclodextrin", Chinese Journal of Pharmaceuticals, 2006.

* cited by examiner (b) Closed Form  (a) Open Form (c)  (d)

(a) Side View                    (b) Primary Face View (a) Side View           (b) Primary Face View (a) Side View           (b) Primary Face View (a)

(b)

COMPOSITION FOR IMPROVING THE SOLUBILITY OF POORLY SOLUBLE SUBSTANCES, USE THEREOF AND COMPLEX FORMULATION CONTAINING THEREOF

CROSS REFERENCE TO RELATED APPLICATION

This application claims the benefit of U.S. Provisional Application No. 62/610,509, filed on Dec. 26, 2017, the entirety of which is incorporated by reference herein.

The present application is based on, and claims priority from, EP Application Serial Number 18215590.3, filed on Dec. 21, 2018, the disclosure of which is hereby incorporated by reference herein in its entirety.

TECHNICAL FIELD

The present disclosure is related to a composition for improving the solubility of poorly soluble substances, the use thereof, and a complex formulation containing the composition for improving the solubility of poorly soluble substances.

BACKGROUND

Because cyclodextrin can improve the solubility of poorly soluble drugs or avoid drug degradation, it has become an important pharmaceutical excipient at present.

Cyclodextrin molecules are easily bonded to each other by forming intermolecular hydrogen bonds, but such bonding easily blocks the insertion of drug molecules into the cavity of cyclodextrin, thereby causing a decrease in the drug loading amount of the cyclodextrin. Moreover, if the use of cyclodextrin in medical applications is too high, it is likely to result in a potential risk of toxicity, and that limits the amount of cyclodextrin that can be used in many drug formulations.

It is currently known that the efficiency of the inclusion effect of cyclodextrin and drugs can be improved by modifying different functional groups on cyclodextrin, adding appropriate water-soluble polymers, or the like. However, many drugs are still inefficient in forming inclusion with the existing cyclodextrins, in which the molecular size of the drug and the inner ring size of the cyclodextrin are still the main factors determining the inclusion strength of the drug and cyclodextrin.

Therefore, developing a technology capable of enhancing the inclusion effects of cyclodextrin and drugs is still needed in the current field of medical applications.

SUMMARY

The present disclosure provides a composition for improving the solubility of poorly soluble substances, comprising about 40-99.5% by weight of cyclodextrin and/or a derivative thereof, about 0.05-10% by weight of at least one water-soluble polymer, and about 0.05-60% by weight of at least one water-soluble stabilizer.

The present disclosure also provides a use of a composition for improving the solubility of poorly soluble substances, in which the composition comprises about 40-99.5% by weight of cyclodextrin and/or a derivative thereof, about 0.05-10% by weight of at least one water-soluble polymer, and about 0.05-60% by weight of at least one water-soluble stabilizer.

The present disclosure further provides a complex formulation, comprising about 0.05-10% by weight of at least one active ingredient, in which the at least one active ingredient is a hydrophobic compound, about 40-99.5% by weight of cyclodextrin and/or a derivative thereof, about 0.05-10% by weight of at least one water-soluble polymer, and about 0.05-60% by weight of at least one water-soluble stabilizer.

A detailed description is given in the following embodiments with reference to the accompanying drawings.

BRIEF DESCRIPTION OF DRAWINGS

The patent or application file contains at least one color drawing. Copies of this patent or patent application publication with color drawing will be provided by the USPTO upon request and payment of the necessary fee.

The present invention can be more fully understood by reading the subsequent detailed description and examples with references made to the accompanying drawings, wherein.

DETAILED DESCRIPTION

Figure 1:
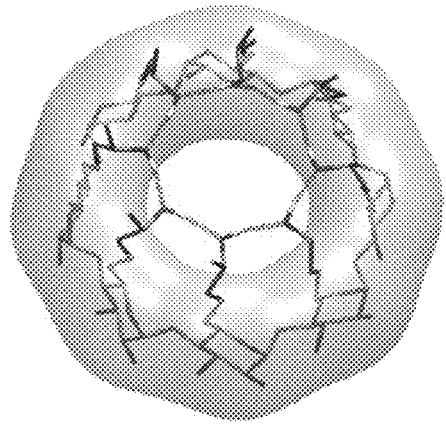
FIG. 1 shows the optimal structures of HPγCD in its closed and open forms: (a) Optimal structures of closed form; (b) optimal structures of open form; (c) a graph highlights the water molecules cannot pass through the closed-form HPγCD; (d) a graph highlights the water molecules can pass through the open-form HPγCD easily.
Figure 1:
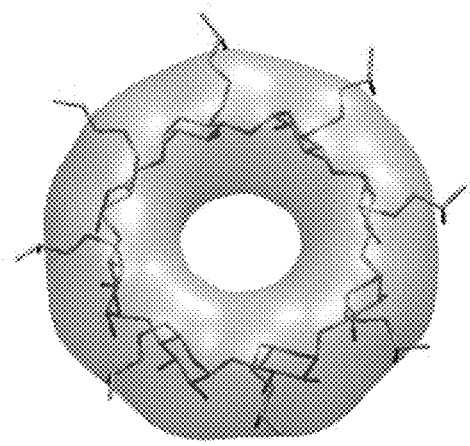
Figure 1:
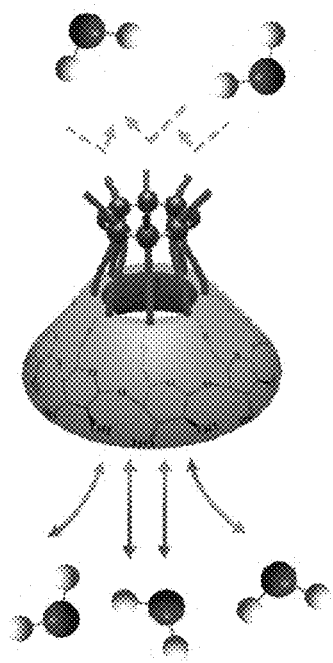
Figure 1:
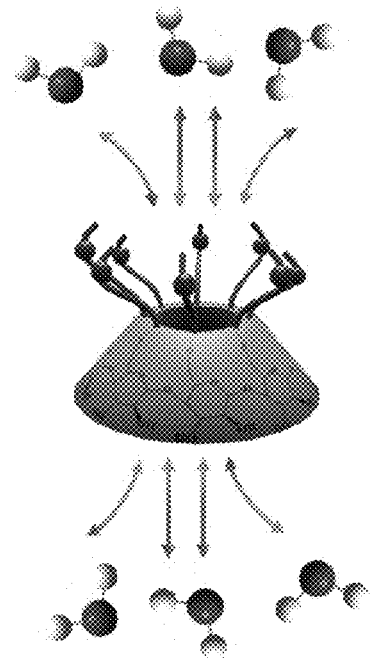
Figure 1:
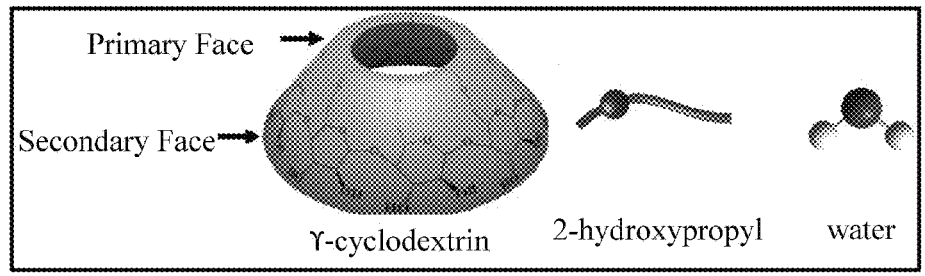

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a composition for improving the solubility of poorly soluble substances. As used herein, "a poorly soluble substance" means any substance having solubility in water of less than about 0.01 g/mL. The above-mentioned poorly soluble substance may comprise, but is not limited to, a hydrophobic compound, for example, may be a hydrophobic drug.

The composition for improving the solubility of poorly soluble substances mentioned above may comprise, but is not limited to cyclodextrin and/or a derivative thereof, at least one water-soluble polymer and at least one water-soluble stabilizer. In the composition for improving the solubility of poorly soluble substances of the present disclosure mentioned above, the content of each component is not particularly limited, and it may be adjusted according to the content of other components, and/or may be adjusted as needed.

In the composition for improving the solubility of poorly soluble substances of the present disclosure mentioned above, the cyclodextrin and/or the derivative thereof may occupy about 40-99.5% by weight, for example may be about 40-45%, 45-50%, 50-55%, 55-60%, 60-65%, 60-65%, 65-70%, 70-75%, 75-80%, 80-85%, 85-90%, 95-99.5%, 55-99.5%, 50-75%, 60-85%, 80-99.5% by weight, but it is not limited thereto.

Examples of the foregoing cyclodextrin may comprise α-cyclodextrin, β-cyclodextrin, γ-cyclodextrin, δ-cyclodextrin or any combination thereof, but they are not limited thereto.

Moreover, examples of the foregoing derivative of cyclodextrin may comprise hydroxypropyl modified cyclodextrin, succinyl modified cyclodextrin, methyl modified cyclodextrin or any combination thereof, but they are not limited thereto. Furthermore, the hydroxypropyl modified cyclodextrin may for example, be hydroxypropyl-γ-cyclodextrin (hydroxypropyl-γ-CD), but it is not limited thereto.

In the composition for improving the solubility of poorly soluble substances of the present disclosure mentioned above, the at least one water-soluble polymer may occupy about 0.05-10% by weight, for example, may be about 0.05-0.1%, 0.05-0.08%, 0.06-0.1%, 0.1-0.12%, 0.15-0.25%, 0.5-1%, 1-2%, 1-3%, 2-5%, 2-3%, 3-5%, 5-7%, 8-10% by weight, but it is not limited thereto.

The molecular weight of the at least one water-soluble polymer mentioned above may be greater than about 2000 Dalton, but is not limited thereto, for example, about 1000-200,000 Dalton. Moreover, the at least one water-soluble polymer mentioned above may comprise, but is not limited to hydroxypropyl methyl cellulose (HPMC), hydroxypropyl cellulose, carboxymethyl cellulose (CMC), polyvinylpyrrolidone, (PVP), polyvinyl alcohol, poly(ethylene glycol)-poly(propylene glycol)-poly(ethylene glycol) (PEG-PPG-PEG (ABA)) triblock copolymer or any combination thereof, etc. In one embodiment, in the composition for improving the solubility of poorly soluble substances of the present disclosure mentioned above, the at least one water-soluble polymer mentioned above may be hydroxypropyl methyl cellulose.

In the composition for improving the solubility of poorly soluble substances of the present disclosure mentioned above, the at least one water-soluble stabilizer may occupy about 0.05-60% by weight, for example, may be about 0.05-0.1%, 0.05-0.08%, 0.06-0.1%, 0.1-0.12%, 0.15-0.25%, 0.5-1%, 1-2%, 1-3%, 2-5%, 2-3%, 3-5%, 5-7%, 8-10%, 10-15%, 15-20%, 20-25%, 25-30%, 30-35%, 35-40%, 40-45%, 40-55%, 45-50%, 50-55%, 55-60% by weight, but it is not limited thereto.

Examples of at least one water-soluble stabilizer mentioned above may comprise, but are not limited thereto, an amino acid with a polar side chain, an oligopeptide containing at least one amino acid with a polar side chain, purine, a derivative of purine or any combination thereof.

The amino acid with a polar side chain mentioned above may be any amino acid having a polar side chain, which may be a natural amino acid or a non-natural amino acid, and is not limited. For instance, examples of the amino acid with a polar side chain may comprise glycine, cysteine, glutamine, glutamic acid or histidine, but they are not limited thereto.

Furthermore, the oligopeptide containing at least one amino acid with a polar side chain mentioned above is only required to contain at least one amino acid with a polar side chain in the amino acids constituting the same, and there is no particular limitation. For example, the oligopeptide containing at least one amino acid with a polar side chain mentioned above may have only one amino acid with a polar side chain, or may have several amino acids, each of which has a polar side chain, or the oligopeptide containing at least one amino acid with a polar side chain mentioned above may also be entirely composed of amino acids, each of which has a polar side chain. Moreover, each amino acid contained by the oligopeptide containing at least one amino acid with a polar side chain mentioned above may independently be any kind of amino acid, as long as the amino acids constituting the oligopeptide containing at least one amino acid with a polar side chain. In addition, in the oligopeptide containing at least one amino acid with a polar side chain mentioned above, the position of the at least one amino acid with a polar side chain in the oligopeptide is also not particularly limited, and it can independently be anywhere in the oligopeptide. The at least one amino acid with a polar side chain in the foregoing oligopeptide may independently comprise glycine, cysteine, glutamine, glutamic acid, histidine, any combination thereof, etc., but it is not limited thereto.

In one embodiment, the foregoing oligopeptide containing at least one amino acid with a polar side chain may have about 2-8 amino acids, such as 2-3, 2-6, 2, 3, 4, 5, 6, 7, 8 amino acids, but it is not limited thereto. Moreover, examples of the foregoing oligopeptide containing at least one amino acid with a polar side chain may be listed as carnosine, glutathione (GSH), leucine-glycine-glycine (Leu-Gly-Gly), or the like, but it is not limited thereto.

Moreover, examples of the foregoing purine may comprise adenine, guanine, a combination thereof, but they are not limited thereto. The foregoing derivative of purine may comprise, but is not limited to caffeine, theobromine, isoguanine, xanthine, hypoxanthine, uric acid, any combination thereof, etc.

In one embodiment, in the composition for improving the solubility of poorly soluble substances of the present disclosure mentioned above, the at least one water-soluble stabilizer mentioned above may be, but is not limited to, the amino acid with a polar side chain, such as glycine, glutamine, glutamic acid or histidine. In another embodiment, in the composition for improving the solubility of poorly soluble substances of the present disclosure mentioned above, the at least one water-soluble stabilizer mentioned above may be, but is not limited to, the oligopeptide containing at least one amino acid with a polar side chain, such as carnosine, glutathione, leucine-glycine-glycine. In yet another embodiment, in the composition for improving the solubility of poorly soluble substances of the present disclosure mentioned above, the at least one water-soluble stabilizer mentioned above may be, but is not limited to, the derivative of purine, such as caffeine.

In one embodiment, in the composition for improving the solubility of poorly soluble substances of the present disclosure mentioned above, the at least one water-soluble stabilizer mentioned above is the amino acid with a polar side chain or the oligopeptide containing at least one amino acid with a polar side chain while the cyclodextrin and/or the derivative thereof mentioned above may occupy about 40-85% by weight, the at least one water-soluble polymer mentioned above may occupy about 0.5-5% by weight, and the amino acid with a polar side chain or the oligopeptide containing at least one amino acid with a polar side chain may occupy about 15-55% by weight. Furthermore, the cyclodextrin and/or the derivative thereof mentioned above may be hydroxypropyl-γ-cyclodextrin, and the at least one water-soluble polymer mentioned above may be hydroxypropyl methyl cellulose.

Moreover, in the composition for improving the solubility of poorly soluble substances of the present disclosure mentioned above, for one specific embodiment, under the premise that the at least one water-soluble stabilizer mentioned above is the amino acid with a polar side chain or the oligopeptide containing at least one amino acid with a polar side chain, and the cyclodextrin and/or the derivative thereof, the at least one water-soluble polymer and the amino acid with a polar side chain or the oligopeptide containing at least one amino acid with a polar side chain may respectively occupy about 40-85% by weight, 0.5-5% by weight and 15-55% by weight, if it is further limited to that the cyclodextrin and/or the derivative thereof may be hydroxypropyl-γ-cyclodextrin, the at least one water-soluble polymer may be hydroxypropyl methyl cellulose, and the at least one water-soluble stabilizer may be the amino acid with a polar side chain, and the amino acid with a polar side chain may comprise glutamine, glutamic acid or histidine, in this specific embodiment, the foregoing hydroxypropyl-γ-cyclodextrin may occupy about 70-85% by weight, the foregoing hydroxypropyl methyl cellulose may occupy about 0.5-3% by weight, and the foregoing amino acid with a polar side chain may occupy about 10-25% by weight.

Alternatively, in the composition for improving the solubility of poorly soluble substances of the present disclosure mentioned above, for one specific embodiment, under the premise that the at least one water-soluble stabilizer mentioned above is the amino acid with a polar side chain or the oligopeptide containing at least one amino acid with a polar side chain, and the cyclodextrin and/or the derivative thereof, the at least one water-soluble polymer and the amino acid with a polar side chain or the oligopeptide containing at least one amino acid with a polar side chain may respectively occupy about 40-85% by weight, 0.5-5% by weight, and 15-55% by weight, if it is further limited to that the cyclodextrin and/or the derivative thereof may be hydroxypropyl-γ-cyclodextrin, the at least one water-soluble polymer may be hydroxypropyl methyl cellulose, and the at least one water-soluble stabilizer is oligopeptide containing at least one amino acid with a polar side chain, and the oligopeptide containing at least one amino acid with a polar side chain may comprise carnosine, glutathione or leucine-glycine-glycine, in this specific embodiment, the foregoing hydroxypropyl-γ-cyclodextrin may occupy about 40-80% by weight, the foregoing hydroxypropyl methyl cellulose may occupy about 0.5-3% by weight, and the foregoing oligopeptide containing at least one amino acid with a polar side chain may occupy about 15-55% by weight.

In another embodiment, in the composition for improving the solubility of poorly soluble substances of the present disclosure mentioned above, the at least one water-soluble stabilizer mentioned above may be the derivative of purine, the derivative of purine may be caffeine, the cyclodextrin and/or the derivative thereof mentioned above may be hydroxypropyl-γ-cyclodextrin, and the at least one water-soluble polymer mentioned above may be hydroxypropyl methyl cellulose. In one specific embodiment of this embodiment, the foregoing hydroxypropyl-γ-cyclodextrin may occupy about 70-99.5% by weight, the foregoing hydroxypropyl methyl cellulose may occupy about 0.1-5% by weight, and the foregoing caffeine may occupy about 0.05-20% by weight.

Furthermore, in one embodiment, the composition for improving the solubility of poorly soluble substances of the present disclosure mentioned above, in addition to the cyclodextrin and/or the derivative thereof, the at least one water-soluble polymer and the at least one water-soluble stabilizer mentioned above, may further comprise a solvent to form a solution with the cyclodextrin and/or the derivative thereof, the at least one water-soluble polymer and the at least one water-soluble stabilizer mentioned above. In this solution, the total concentration of the cyclodextrin and/or the derivative thereof, the at least one water-soluble polymer and the at least one water-soluble stabilizer may be about 5-55% (w/v), for example, may be 5-10%, 10-20%, 20-25%, 30-35%, 35-40%, 40-45%, 45-50, 50-55, but it is not limited thereto.

The present disclosure also provides a use of a composition for improving the solubility of poorly soluble substances. In the use of a composition for improving the solubility of poorly soluble substances, the said composition may be any composition for improving the solubility of poorly soluble substances of the present disclosure mentioned above. Furthermore, since the description of the poorly soluble substances, the cyclodextrin and/or the derivative thereof, the at least one water-soluble polymer and the at least one water-soluble stabilizer has been described in the relevant paragraphs of the composition for improving the solubility of poorly soluble substances of the present disclosure mentioned above, it will not be repeatedly described herein.

In the use of a composition for improving the solubility of poorly soluble substances, compared with dissolving the poorly soluble substances in an aqueous solvent, dissolving the poorly soluble substance in an aqueous solvent together with the said composition improves the solubility of the poorly soluble substances.

The present disclosure may further provide a complex formulation. The complex formulation of the present disclosure mentioned above may comprise, but is not limited to, at least one active ingredient, cyclodextrin and/or a derivative thereof, at least one water-soluble polymer and the at least one water-soluble stabilizer, in which the at least one active ingredient is a hydrophobic compound. In the complex formulation of the present disclosure mentioned above, the content of each component is not particularly limited, and it may be adjusted according to the content of other components, and/or may be adjusted as needed.

In the complex formulation of the present disclosure mentioned above, the cyclodextrin and/or the derivative thereof, the at least one water-soluble polymer and the at least one water-soluble stabilizer can be regarded as the components of the composition for improving the solubility of a poorly soluble substance of the present disclosure mentioned above, which has an effect of improving the solubility of the active ingredient in the complex formulation of the present disclosure.

In the complex formulation of the present disclosure mentioned above, the at least one active ingredient mentioned above may occupy about 0.05-10% by weight, for example, may be about 0.05-0.1%, 0.05-0.08%, 0.06-0.1%, 0.1-0.12%, 0.15-0.25%, 0.5-1%, 1-2%, 1-3%, 2-5%, 2-3%, 3-5%, 5-7%, 8-10% by weight, but it is not limited thereto.

In one embodiment, the complex formulation of the present disclosure mentioned above may be a pharmaceutical formulation. In the complex formulation of the present disclosure mentioned above, the active ingredient means a hydrophobic ingredient that has a therapeutic, alleviating and/or prophylactic effect on a disease and/or a symptom, but it is not limited thereto.

As used herein, "a hydrophobic compound" means any substance having solubility in water of less than about 0.01 g/mL, but it is not limited thereto. The above-mentioned hydrophobic compound may comprise a steroid drug, an aromatic compound with a molecular weight of 100-1000 Da or any combination thereof, etc., but it is not limited thereto.

Examples of the steroid drug may comprise, but it is not limited to, loteprednol etabonate, dexamethasone, dexamethasone phosphate, prednisolone, prednisolone acetate, fluorometholone, 17β-estradiol, 17α-ethinylestradiol, ethinylestradiol 3-methyl ether, estriol, norethindrone, norethindrone acetate, norgestrel, ethisterone, methoxyprogesterone, progesterone, 17-methyltestosterone, triamcinolone, testosterone, spironolactone, alfaxalone, lanostanoid or any combination thereof.

Moreover, the aromatic compound with a molecular weight of 100-1000 Da may comprise axitinib, methotrexate, folic acid, diclofenac sodium, lutein, any combination thereof, etc., but it is not limited thereto.

In the complex formulation of the present disclosure mentioned above, the cyclodextrin and/or the derivative thereof may occupy about 40-99.5% by weight, such as 40-45%, 45-50%, 50-55%, 55-60%, 60-65%, 60-65%, 65-70%, 70-75%, 75-80%, 80-85%, 85-90%, 95-99.5%, 55-99.5%, 50-75%, 60-85%, 80-99.5% by weight, but it is not limited thereto.

Furthermore, since the description of the cyclodextrin and/or the derivative thereof in the complex formulation has been described in the relevant paragraphs of the composition for improving the solubility of poorly soluble substances of the present disclosure mentioned above, it will not be repeatedly described herein.

In the complex formulation of the present disclosure mentioned above, the at least one water-soluble polymer may occupy about 0.05-10% by weight, such as about 0.05-0.1%, 0.05-0.08%, 0.06-0.1%, 0.1-0.12%, 0.15-0.25%, 0.5-1%, 1-2%, 1-3%, 2-5%, 2-3%, 3-5%, 5-7%, 8-10% by weight, but it is not limited thereto.

Moreover, since the description of the at least one water-soluble polymer in the complex formulation also has been described in the relevant paragraphs of the composition for improving the solubility of poorly soluble substances of the present disclosure mentioned above, it will not be repeatedly described herein.

Furthermore, in the complex formulation of the present disclosure mentioned above, the at least one water-soluble stabilizer may occupy about 0.05-60% by weight, such as about 0.05-0.1%, 0.05-0.08%, 0.06-0.1%, 0.1-0.12%, 0.15-0.25%, 0.5-1%, 1-2%, 1-3%, 2-5%, 2-3%, 3-5%, 5-7%, 8-10%, 10-15%, 15-20%, 20-25%, 25-30%, 30-35%, 35-40%, 40-45%, 40-55%, 45-50%, 50-55%, 55-60% by weight, but it is not limited thereto Similarly, since the description of the at least one water-soluble stabilizer in the complex formulation has been described in the relevant paragraphs of the composition for improving the solubility of poorly soluble substances of the present disclosure mentioned above, it will not be repeatedly described herein.

In one embodiment, in the complex formulation of the present disclosure mentioned above, the at least one water-soluble stabilizer mentioned above is the amino acid with a polar side chain or the oligopeptide containing at least one amino acid with a polar side chain, and the active ingredient mentioned above may occupy about 0.5-5% by weight, cyclodextrin and/or a derivative thereof mentioned above may occupy about 40-85% by weight, the at least one water-soluble polymer mentioned above may occupy about 0.5-5% by weight, and the amino acid with a polar side chain or the oligopeptide containing at least one amino acid with a polar side chain mentioned may occupy about 15-55% by weight. Furthermore, the active ingredient mentioned above may be loteprednol etabonate or axitinib, the cyclodextrin and/or a derivative thereof mentioned above may be hydroxypropyl-γ-cyclodextrin, and the at least one water-soluble polymer mentioned above may be hydroxypropyl methyl cellulose.

Furthermore, in the complex formulation of the present disclosure mentioned above, for one specific embodiment, under the premise that the at least one water-soluble stabilizer mentioned above is the amino acid with a polar side chain or the oligopeptide containing at least one amino acid with a polar side chain, and the cyclodextrin and/or the derivative thereof, the at least one water-soluble polymer, and the amino acid with a polar side chain or the oligopeptide containing at least one amino acid with a polar side chain may respectively occupy about 40-85% by weight, 0.5-5% by weight, and 15-55% by weight, if it is further limited to that the active ingredient may be loteprednol etabonate or axitinib, the cyclodextrin and/or the derivative thereof may be hydroxypropyl-γ-cyclodextrin, the at least one water-soluble polymer may be hydroxypropyl methyl cellulose, and the at least one water-soluble stabilizer may be amino acid with a polar side chain, and the amino acid with a polar side chain may comprise glutamine, glutamic acid or histidine, in this specific embodiment, the foregoing loteprednol etabonate or axitinib may occupy about 0.1-3%, the foregoing hydroxypropyl-γ-cyclodextrin may occupy about 70-85%, the foregoing hydroxypropyl methyl cellulose may occupy about 0.5-3%, and the foregoing amino acid with a polar side chain may occupy about 10-25%.

Alternatively, in the complex formulation of the present disclosure mentioned above, for one specific embodiment, under the premise that the at least one water-soluble stabilizer mentioned above is the amino acid with a polar side chain or the oligopeptide containing at least one amino acid with a polar side chain, the cyclodextrin and/or the derivative thereof, the at least one water-soluble polymer, and the amino acid with a polar side chain or the oligopeptide containing at least one amino acid with a polar side chain may respectively occupy about 40-85%, 0.5-5%, and 15-55% by weight, if it is further limited to that the active ingredient may be loteprednol etabonate or axitinib, the cyclodextrin and/or the derivative thereof may be hydroxypropyl-γ-cyclodextrin, the at least one water-soluble polymer may be hydroxypropyl methyl cellulose, and the at least one water-soluble stabilizer may be oligopeptide containing at least one amino acid with a polar side chain, and oligopeptide containing at least one amino acid with a polar side chain may comprise carnosine, glutathione or leucine-glycine-glycine, in this specific embodiment, the foregoing loteprednol etabonate or axitinib may occupy about 0.1-3% by weight, the foregoing hydroxypropyl-γ-cyclodextrin may occupy about 40-80% by weight, the foregoing hydroxypropyl methyl cellulose may occupy about 0.5-3% by weight, and the foregoing oligopeptide containing at least one amino acid with a polar side chain may occupy about 15-55% by weight.

In another embodiment, in the complex formulation of the present disclosure mentioned above, the at least one water-soluble stabilizer mentioned above may be the derivative of purine, and the derivative of purine may be caffeine, and the active ingredient mentioned above may be loteprednol etabonate or axitinib, the cyclodextrin and/or the derivative thereof mentioned above may be hydroxypropyl-γ-cyclodextrin, and the at least one water-soluble polymer mentioned above may be hydroxypropyl methyl cellulose. In one specific embodiment of this embodiment, the foregoing loteprednol etabonate or axitinib may occupy about 1.5-5% by weight, the foregoing hydroxypropyl-γ-cyclodextrin may occupy about 70-99.5% by weight, the foregoing hydroxypropyl methyl cellulose may occupy about 0.1-5% by weight, and the foregoing caffeine may occupy about 0.05-20% by weight.

Furthermore, the complex formulation of the present disclosure, in addition to the active ingredient, the cyclodextrin and/or the derivative thereof, the at least one water-soluble polymer and the at least one water-soluble stabilizer, may further comprise a surfactant to make the complex formulation form a microparticle. In the complex formulation of the present disclosure mentioned above, the at least one active ingredient may occupy about 0.05-10% by weight, the cyclodextrin and/or the derivative thereof may occupy about 40-99.5% by weight, the at least one water-soluble polymer may occupy 0.05-10% by weight, the water-soluble stabilizer may occupy 0.05-60% by weight, and the surfactant may occupy 0.05-10% by weight, but it is not limited thereto.

The surfactant may comprise, but is not limited to Tween 80, Tween 20, Span 80, DSPE-PEG, a derivative of DSPE-PEG or any combination thereof. In one embodiment, the surfactant may be Tween 80. In another embodiment, the surfactant may be a combination of Tween 80 and DSPE-PEG.

The average particle size of the microparticle may be 500 nm-100 μm, for example, may be about 500 nm-800 nm, 800 nm-1000 nm, 10 μm-50 μm, 50 μm-100 μm, but it is not limited thereto.

In one embodiment, the at least one active ingredient may be loteprednol etabonate or axitinib, and the surfactant may be Tween 80. Moreover, in this embodiment, the loteprednol etabonate or axitinib may occupy about 0.01-10% by weight, the cyclodextrin and/or the derivative thereof may occupy about 50-90% by weight, the at least one water-soluble polymer may occupy 0.05-20% by weight, the water-soluble stabilizer may occupy 0.05-20% by weight, and Tween 80 may occupy 0.1-10% by weight, but it is not limited thereto.

Moreover, the complex formulation of the present disclosure, in addition to the active ingredient, the cyclodextrin and/or a derivative thereof, the at least one water-soluble polymer and the at least one water-soluble stabilizer mentioned above, may further comprise a solvent to form a liquid dosage form with the at least one active ingredient, the cyclodextrin and/or the derivative thereof, the at least one water-soluble polymer and the at least one water-soluble stabilizer. In this liquid dosage form, the total concentration of the cyclodextrin and/or the derivative thereof, the at least one water-soluble polymer and the at least one water-soluble stabilizer may be about 5-55% (w/v), for example, may be 5-10%, 10-20%, 20-25%, 30-35%, 35-40%, 40-45%, 45-50%, 50-55%, but it is not limited thereto.

The solvent mentioned above may comprise, but is not limited to water, ethanol or a water/ethanol mixture, etc.

In one embodiment, the complex formulation may form a liquid dosage form, and the complex formulation may be a pharmaceutical formulation. The type of the liquid dosage form mentioned above may comprise, but is not limited to, an oral dosage form, an injection dosage form, an eye drop, etc. Moreover, examples of the injection dosage form mentioned above may comprise, but is not limited to, a subcutaneous injection dosage form, an intramuscular injection dosage form or an intraperitoneal injection dosage form. In one embodiment, the liquid dosage form of the complex formulation of the present disclosure is an eye drop.

In addition, the complex formulation may be administered to a subject in need of the complex formulation, but it is not limited thereto. The administration route of the complex formulation of the present disclosure may be administered parenterally, orally, by an inhalation spray, or via an implanted reservoir, but is not limited thereto. The parenteral methods may comprise, but is not limited to, smearing the affected regions, subcutaneous, intracutaneous, intravenous, intramuscular, intra-articular, intra-arterial, intrasynovial, intrasternal, intrathecal, and intraleaional injection, intraocular injection, eye drops, as well as infusion techniques, etc.

Furthermore, the foregoing subject may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

EXAMPLES

Example 1

Solubility Test for Loteprednol Etabonate (LE)

Example 1-1

Effect of using different amino acids, oligopeptides or monosaccharide as a stabilizer of a formulation on the solubility of the drug (loteprednol etabonate) in a formulation containing loteprednol etabonate (LE)/hydroxypropyl-γ-cyclodextrin (HPγCD)

1. Method

The samples were formulated and analyzed according to the formulas shown in the following Table 1 and the methods described below at room temperature.

Hydroxypropyl-γ-cyclodextrin, a water-soluble polymer (hydroxypropyl methyl cellulose (HPMC (molecular weight: 16676)) and an amino acid (glutamine (Gln), glutamic acid (Glu) or histidine (His)) or an oligopeptide (glutathione (GSH), L-carnosine or leucine-glycine-glycine (Leu-Gly-Gly)) as a stabilizer of the formulation were dissolved in 3 mL of deionized water to form a solution, and groups using an oligopeptide (glycine-glycine (Gly-Gly)) and monosaccharide (mannitol) as stabilizers of the formulations were served as the negative control groups.

Next, in an ultrasonic water bath environment, the above solution was slowly added to a methanol solution containing 4 mg loteprednol etabonate (LE) (10 mg LE/mL) to form a mixture. After that, the mixture was dried in a vacuum environment to performing drying to remove the solvent therein and obtain a dried product.

Thereafter, the dried product was re-dissolved in 2 mL of deionized water to form a test sample, and the test sample solution was adjusted to pH 5.5 with 1 M NaOH. Next, the test sample was filtered with a 0.22 μm pore size filter to remove undissolved precipitate. Finally, the content of loteprednol etabonate (LE) in the test sample was analyzed by high performance liquid chromatography (HPLC).

TABLE 1

| Sample | LE (mg) | HPγCD (mg) | HPMC (mg) | Stabilizer (mg) |
|---|---|---|---|---|
| LE | 4 | 0 | 0 | 0 |
| LE/GSH | 4 | 0 | 0 | 120 |
| LE/HPMC | 4 | 0 | 5 | 0 |
| LE/HPγCD | 4 | 204 | 0 | 0 |
| LE/HPγCD/HPMC | 4 | 204 | 5 | 0 |
| LE/HPγCD/GSH | 4 | 204 | 0 | 120 |
| LE/HPMC/GSH | 4 | 0 | 5 | 120 |
| LE/HPγCD/HPMC/GSH | 4 | 204 | 5 | 120 |
| LE/HPγCD/HPMC/Gln | 4 | 204 | 5 | 57.06 |
| LE/HPγCD/HPMC/Glu | 4 | 204 | 5 | 57.44 |
| LE/HPγCD/HPMC/His | 4 | 204 | 5 | 60.59 |
| LE/HPγCD/HPMC/Carnosine | 4 | 204 | 5 | 88.34 |
| LE/HPγCD/HPMC/Leu-Gly-Gly | 4 | 204 | 5 | 95.78 |
| LE/HPγCD/HPMC/Gly-Gly | 4 | 204 | 5 | 51.58 |
| LE/HPγCD/HPMC/Mannitol | 4 | 204 | 5 | 71.13 |

2. Results

The solubility of loteprednol etabonate (LE) of each sample and the degree of solubility improvement compared to loteprednol etabonate (LE)/HPγCD are as shown in Table 2 below.

TABLE 2

| Sample | LE feeding (μg) | Solubility of LE (μg/mL) | Fold of solubility relative to LE/HPγCD |
|---|---|---|---|
| LE | 4000 | 1.5 | N.A. |
| LE/GSH | 4000 | 1.5 | N.A. |
| LE/HPMC | 4000 | 3.4 | N.A. |
| LE/HPγCD | 4000 | 290.7 | 1.00 |
| LE/HPγCD/HPMC | 4000 | 1010.6 | 3.48 |
| LE/HPγCD/GSH | 4000 | 331.4 | 1.14 |
| LE/HPMC/GSH | 4000 | 1.8 | N.A. |
| LE/HPγCD/HPMC/GSH | 4000 | 1885.4 | 6.49 |
| LE/HPγCD/HPMC/Gln | 4000 | 1806.1 | 6.21 |
| LE/HPγCD/HPMC/Glu | 4000 | 1705.5 | 5.87 |
| LE/HPγCD/HPMC/His | 4000 | 1634.2 | 5.62 |
| LE/HPγCD/HPMC/Carnosine | 4000 | 1827.9 | 6.29 |
| LE/HPγCD/HPMC/Leu-Gly-Gly | 4000 | 1551.2 | 5.34 |
| LE/HPγCD/HPMC/Gly-Gly | 4000 | 800.0 | 2.75 |
| LE/HPγCD/HPMC/Mannitol | 4000 | 1025.0 | 6.60 |

N.A.: Not detected

According to Table 2 above, it can be known that the water solubility of LE is extremely low, only 1.5 μg/mL. Similarly, when LE is only mixed with the water-soluble polymer, HPMC, or the formulation stabilizer, GSH, the solubility of LE in an aqueous solution still cannot be effectively improved. Only mixing LE with HPγCD can improve the solubility of LE in an aqueous solution, and that increases from less than 4 μg/mL to 290 μg/mL.

Moreover, when the formula of LE/HPγCD was further mixed with the water-soluble polymer, HPMC, or the formulation stabilizer, GSH, respectively, the LE solubility may be about 1.2-3.5 times that of the combination of LE/HPγCD.

Furthermore, when LE was mixed together with HPγCD, the water-soluble polymer, HPMC, and the formulation stabilizer (amino acid or oligopeptide), the solubility of LE could be further improved, for example, LE solubility of LE/HPγCD/HPMC/GSH formula might be 6.5 times that of the LE/HPγCD formula.

In addition, according to the test results of a plurality of different formulations, it is shown that specific amino acids and oligopeptides can effectively improve the solubility of LE in the formulation, and among them, using glutamine and glutamic acid (amino acid) and carnosine and glutathione (oligopeptide) as a formulation stabilizer can significantly improve the solubility of LE which may be about 5.3-6.6 times that of LE/HPγCD. In contrast, the stability of the sample, LE/HPγCD/HPMC/mannitol, was not good, and it precipitated rapidly within 1 hour.

Example 1-2

Effect of using histidine (His) as a stabilizer of a formulation on the solubility of the drug (loteprednol etabonate) in a formulation containing loteprednol etabonate (LE)/hydroxypropyl-γ-cyclodextrin (HPγCD)

1. Method

The samples were formulated and analyzed according to the formulas shown in the following Table 3 and the methods described below at room temperature.

Hydroxypropyl-γ-cyclodextrin, a water-soluble polymer (hydroxypropyl methyl cellulose (HPMC) (molecular weight: 16676)), and histidine (His) as a stabilizer of the formulation were co-dissolved in secondary water to form a solution.

Next, the above solution was slowly added to a methanol solution containing loteprednol etabonate (LE) to form a mixture. After that, the mixture was treated by a rotary evaporator to completely remove methanol, and the pH was adjusted to 5.5 with a 0.1 M HCl aqueous solution, and the final solution volume was fixed to 1 mL (the insufficient portion was replenished with secondary water) to form a test sample. Thereafter, the test sample was then filtered with a 0.22 μm pore size filter to remove undissolved precipitate. Finally, the content of loteprednol etabonate (LE) in the test sample was analyzed by high performance liquid chromatography (HPLC).

TABLE 3

| Number | Sample | LE (mg) | HPγCD (mg) | His (mg) | HPMC (mg) | Solubility of LE (μg/mL) |
|---|---|---|---|---|---|---|
| 1 | LE | 8 | — | — | — | 1.5 |
| 2 | LE/2HPγCD/His/HPMC | 8 | 408 | — | — | 807.1 |
| 3 | LE/2HPγCD/His/HPMC | 6 | 408 | 80 | 10 | 5162.7 |

—: No addition

2. Results

The solubility of loteprednol etabonate (LE) of each sample and the degree of solubility improvement compared to loteprednol etabonate (LE)/HPγCD are as shown in Table 4 below.

TABLE 4

| Number | Sample | The amount of LE that can be loaded per unit of HPγCD (μg/mg) | Fold of solubility relative to LE/2HPγCD |
|---|---|---|---|
| 1 | LE | N.A. | N.A. |
| 2 | LE/2HPγCD | 2.0 | 1.0 |
| 3 | LE/2HPγCD/His/HPMC | 12.7 | 6.4 |

N.A.: Not detected

According to Table 4, it can be known that in the LE/2HPγCD (Sample 2) formulation, the range of the amount of LE that can be loaded per unit of HPγCD is about 2.0 (μg/mg). However, when the water-soluble polymer, HPMC, and the formulation stabilizer, histidine, (LE/2HPγCD/His/HPMC, Sample 3) were added, the range of the amount of drug that can be loaded per unit of HPγCD was significantly increased to 12.7 (μg/mg). Namely, the solubility of LE added to the formulation of the water-soluble polymer, HPMC, and the formulation stabilizer, histidine, was 6.4 times that of Sample 2 (LE/2HPγCD formulation).

Example 1-3

Effect of using glutathione (GSH) as a stabilizer of a formulation on the solubility of the drug (loteprednol etabonate) in a formulation containing loteprednol etabonate (LE)/hydroxypropyl-γ-cyclodextrin (HPγCD)

1. Method

The samples were formulated and analyzed according to the formula shown in the following Table 5 and the methods described below at room temperature.

Hydroxypropyl-γ-cyclodextrin, a water-soluble polymer (hydroxypropyl methyl cellulose (HPMC) (molecular weight: 16676)), and glutathione (GSH) as a stabilizer of the formulation were co-dissolved in secondary water to form a solution.

Next, the above solution was slowly added to a methanol solution containing loteprednol etabonate (LE) to form a mixture. After that, the mixture was treated by a rotary evaporator to completely remove methanol, and the pH was adjusted to 5.5 with a 1 M NaOH aqueous solution, and the final solution volume was fixed to 1 mL (the insufficient portion was replenished with secondary water) to form a test sample. Thereafter, the test sample was then filtered with a 0.22 μm pore size filter to remove undissolved precipitate. Finally, the content of loteprednol etabonate (LE) in the test sample was analyzed by high performance liquid chromatography (HPLC).

TABLE 5

| Number | Sample | LE (mg) | HPγCD (mg) | GSH (mg) | HPMC (mg) | Solubility of LE (μg/mL) |
|---|---|---|---|---|---|---|
| 1 | LE | 4 | — | — | — | 1.5 |
| 2 | LE/GSH | 4 | — | 240 | — | 2.0 |
| 3 | LE/HPMC | 4 | — | — | 5 | 3.4 |
| 4 | LE/HPγCD | 4 | 204 | — | — | 290.7 |
| 5 | LE/HPγCD/GSH/HPMC | 4 | 204 | 160 | 5 | 1517.1 |
| 6 | LE/HPγCD/1.5GSH/HPMC | 4 | 204 | 240 | 5 | 1080.4 |

—: No addition

2. Results

The solubility of loteprednol etabonate (LE) of each sample and the degree of solubility improvement compared to loteprednol etabonate (LE)/HPγCD are as shown in Table 6 below.

TABLE 6

| Number | Sample | The amount of LE that can be loaded per unit of HPγCD (μg/mg) | Fold of solubility relative to LE/HPγCD |
|---|---|---|---|
| 1 | LE | N.A. | N.A. |
| 2 | LE/GSH | N.A. | N.A. |
| 3 | LE/HPMC | N.A. | N.A. |
| 4 | LE/HPγCD | 1.4 | 1.0 |
| 5 | LE/HPγCD/GSH/HPMC | 7.4 | 5.2 |
| 6 | LE/HPγCD/1.5GSH/HPMC | 5.3 | 3.7 |

N.A.: Not detected

According to Table 6, it can be known that in the LE/HPγCD (Sample 4) formulation, the range of the amount of LE that can be loaded per unit of HPγCD is about 1.4 (μg/mg). However, when the water-soluble polymer, HPMC, and the formulation stabilizer, glutathione (GSH), (Sample 5 and Sample 6) were added, the range of the amount of drug that can be loaded per unit of HPγCD was significantly increased to 5.3-7.4 (μg/mg). Namely, the solubility of LE added to the formulation of the water-soluble polymer, HPMC, and the formulation stabilizer, glutathione (GSH), was about 3.7-5.2 times that of Sample 4 (LE/HPγCD formulation).

Example 1-4

Effect of using caffeine as a stabilizer of a formulation on the solubility of the drug (loteprednol etabonate) in a formulation containing loteprednol etabonate (LE)/hydroxypropyl-γ-cyclodextrin (HPγCD)

1. Method

The samples were formulated and analyzed according to the formula shown in the following Table 7 and the methods described below at room temperature.

Hydroxypropyl-γ-cyclodextrin, a water-soluble polymer (hydroxypropyl methyl cellulose (HPMC), and caffeine as a stabilizer of the formulation were co-dissolved in secondary water to form a solution.

Next, the above solution was slowly added to a methanol solution containing loteprednol etabonate (LE) to form a mixture. After that, the mixture was treated by a rotary evaporator to completely remove methanol, and the pH was adjusted to 5.5 with a 0.1 M citric acid aqueous solution, and the final solution volume was fixed to 1 mL (the insufficient portion was replenished with secondary water) to form a test sample. Thereafter, the test sample was then filtered with a 0.22 μm pore size filter to remove undissolved precipitate. Finally, the content of loteprednol etabonate (LE) in the test sample was analyzed by high performance liquid chromatography (HPLC).

TABLE 7

| Sample number | LE (mg) | HPγCD (mg) | Caffeine (mg) | HPMC (mg) | pH | Volume (mL) | LE Content (μg/mL) |
|---|---|---|---|---|---|---|---|
| 1 | 8 | — | — | — | 5.5 | 1 | 1.5 |
| 2 | 8 | 102 | — | — | 5.5 | 1 | 138.0 |
| 3 | 8 | 204 | — | — | 5.5 | 1 | 341.0 |
| 4 | 8 | 408 | — | — | 5.5 | 1 | 807.1 |
| 5 | 12 | 408 | 50 | 10 | 5.5 | 1 | 5173.8 |
| 6 | 12 | 408 | 5 | 10 | 5.5 | 1 | 6706.7 |
| 7 | 12 | 408 | 1 | 10 | 5.5 | 1 | 5622.5 |
| 8 | 12 | 408 | 5 | — | 5.5 | 1 | 684.1 |
| 9 | 12 | 408 | 5 | 2 | 5.5 | 1 | 5184.0 |

—: No addition

2. Results

The solubility of loteprednol etabonate (LE) of each sample and the degree of solubility improvement compared to loteprednol etabonate (LE)/HPγCD are as shown in Table 8 below.

TABLE 8

| Sample number | The amount of LE that can be loaded per unit of HPγCD (μg/mg) | Fold of solubility relative to LE/HPγCD |
|---|---|---|
| 1 | N.A. | N.A. |
| 2 | 1.4 | 0.7 |
| 3 | 1.7 | 0.9 |
| 4 | 2.0 | 1.0 |
| 5 | 12.7 | 6.4 |
| 6 | 16.4 | 8.2 |
| 7 | 13.8 | 6.9 |
| 8 | 1.7 | 0.9 |
| 9 | 12.7 | 6.4 |

N.A.: Not detected

According to Table 8, it can be known that in the LE/HPγCD formulations (Samples 2, 3, and 4) with different preparation ratios, the concentration of LE per unit HPγCD can be loaded in the range of 1.4-2.0 (μg/mg). However, when the water-soluble polymer, HPMC, and the formulation stabilizer, caffeine, (Samples 5, 6, 7 and 9) were added, the range of the amount of drug that can be loaded per unit of HPγCD was significantly increased to 12.7-16.4 (μg/mg). Namely, the solubility of LE in the formulation of water-soluble polymer, HPMC, and the formulation stabilizer, caffeine, was about 6.4-8.2 times that of Sample 4 (LE/HPγCD formula).

Example 2

Solubility Test for Axitinib

Effect of using caffeine as a stabilizer of a formulation on the solubility of the axitinib in the formulation containing axitinib/hydroxypropyl-γ-cyclodextrin (HPγCD)

1. Method

The samples were formulated and analyzed according to the formula shown in the following Table 9 and the methods described below at room temperature.

Hydroxypropyl-γ-cyclodextrin, a water-soluble polymer (hydroxypropyl methyl cellulose (HPMC)), and caffeine as a stabilizer of the formulation were dissolved in 3 mL of deionized water to form a solution.

Next, in an ultrasonic water bath environment, the above solution was slowly added to an acetic acid solution containing 4.05 mg axitinib (9 mg axitinib/mL) to form a mixture. After that, the mixture was lyophilized to remove the solvent therein and obtain a dried product.

Thereafter, the dried product was re-dissolved in 1 mL of deionized water to form a test sample, and the test sample solution was adjusted to pH 4.3 with 1 M NaOH. Next, the test sample was then filtered with a 0.22 μm pore size filter to remove the undissolved precipitate. Finally, the content of axitinib in the test sample was analyzed by high performance liquid chromatography (HPLC).

TABLE 9

| Sample number | Axitinib (mg) | HPγCD (mg) | HPMC (mg) | Caffeine (mg) |
|---|---|---|---|---|
| 1 | 4.05 | — | — | — |
| 2 | 4.05 | 130.83 | — | — |
| 3 | 4.05 | — | 5 | — |
| 4 | 4.05 | — | — | 30 |
| 5 | 4.05 | 130.83 | 5 | — |
| 6 | 4.05 | 130.83 | — | 30 |
| 7 | 4.05 | — | 5 | 30 |
| 8 | 4.05 | 130.83 | 5 | 30 |

—: No addition

2. Results

The solubility of axitinib of each sample and the degree of solubility improvement compared to axitinib/HPγCD are as shown in Table 10 below.

TABLE 10

| Sample number | Axitinib content (μg/mL) | The amount of axitinib that can be loaded per unit of HPγCD (μg/mg) | Fold of solubility relative to axitinib/HPγCD |
|---|---|---|---|
| 1 | <LOQ (4 μg/mL) | N.A. | N.A. |
| 2 | 105.55 | 8.07 | 1 |
| 3 | 14.55 | N.A. | N.A. |
| 4 | 55.30 | N.A. | N.A. |

TABLE 10-continued

| Sample number | Axitinib content (μg/mL) | The amount of axitinib that can be loaded per unit of HP γCD (μg/mg) | Fold of solubility relative to axitinib/HPγCD |
|---|---|---|---|
| 5 | 375.43 | 2.87 | 3.56 |
| 6 | 226.49 | 1.73 | 2.15 |
| 7 | 270.23 | N.A. | N.A. |
| 8 | 1833.53 | 1.40 | 17.37 |

N.A.: Not detected
LOQ: Limit of quantification

According to Table 10 above, it can be known that the water solubility of axitinib (Sample 1) is extremely low, which is lower than the minimum drug content analytical limit (4 μg/mL). Based on the test result for sample 2, it can be found that when axitinib is mixed with HPγCD, the axitinib content in the solution can be effectively increased to 105.55 μg/mL. Moreover, the test results for the Samples 5 and 6 show that when HPγCD is combined with the water-soluble polymer, HPMC, or the formulation stabilizer, caffeine, the solubility of axitinib can be further improved to 2 to 3.6 times that of the axitinib/HPγCD formulation (Sample 2). Furthermore, if the axitinib/HPγCD formula is combined with the water-soluble polymer, HPMC, and the formulation stabilizer, caffeine, at the same time (Sample 8), the amount of axitinib dissolved can be greatly increased to 1833.53 μg/mL, which about 17.4 times that of the axitinib/HPγCD formula (Sample 2).

Example 3

Molecular Dynamic Simulation of Loteprednol Etabonate/Cyclodextrin/Glutathione Complexation In order to simulate the binding energy and structures of the complexes correctly, the structure of each component including carrier, drug, destabilizer, and stabilizer was optimized first. All geometry optimizations of the component molecules in water (modeled by PCM) were performed using gradient-corrected hybrid density functional theory (DFT) within the Gaussian 16 suite of programs (Frisch, M. J., et al.) on a PC cluster at the National Center for High-Performance Computing, Taiwan. The B3LYP density functional, Becke's three-parameter exchange functional (D. J. Gaussian 16, Wallingford, Conn., 2016) and Lee-Yang-Parr gradient-corrected correlation functional (Becke, A. D., Density-Functional Thermochemistry. III. The Role of Exact Exchange. J. Chem. Phys. 1993, 98, 5648.) were utilized. The moderate-sized 6-31G (d,p) basis set (Lee, C.; Yang, W.; Parr, R. G., Development of the Colle-Salvetti Correlation-Energy Formula Into a Functional of the Electron Density. Physical Review B 1988, 37, 785.) was used. The calculated stable structures were examined in terms of vibrational frequency calculations. The optimized structures are used for the following docking studies.

1. Structure of Hydroxypropyl-γ-Cyclodextrin (HPγCD)

Hydroxypropyl-γ-cyclodextrin (HPγCD), served as the carrier, has two distinct conformations. The hydroxypropyl groups of HPγCD can aggregate together, thereby closing the primary face of HPγCD. The other conformation of HPγCD has its hydroxypropyl groups dispersed in water, thereby opening the primary face of HPγCD. FIG. 1 shows the optimized structures of HPγCD. The closed-form of HPγCD has its hydroxypropyl groups formed hydrogen-bond networks (FIG. 1 (a)), which is 34.7 kcal/mol more stable than the corresponding open form. Therefore, the closed form of HPγCD does not allow the water molecules passing through freely (see FIG. 1 (c)). In contrast, the water molecules can pass through the open form of HPγCD easily (see FIG. 1 (d)). Accordingly, the closed-form of HPγCD was employed for the following studies.

2. Docking Simulations of Inclusion Complexes

Figure 2:
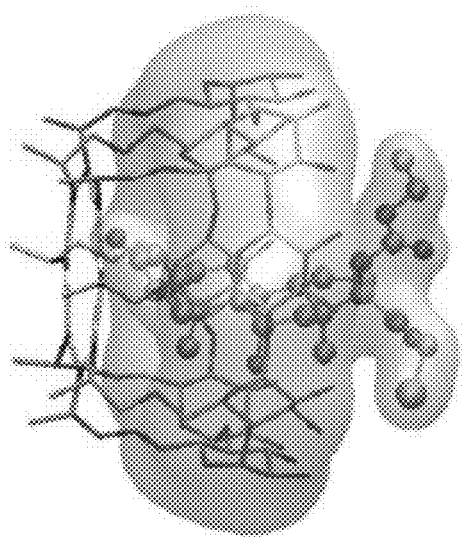
FIG. 2 shows the most stable structure of [LE@HPγCD] inclusion complex obtained from molecular docking analysis.

AutoDock Vina 1.125 was employed to screen the stable structures of the inclusion complexes. Table 11 lists the top 5 docking results of [LE@HPγCD] inclusion complex. The initial structures of LE and HPγCD used for docking simulations are obtained from DFT calculations mentioned above (see previous section). It is observed that the top 5 docking results of [LE@HPγCD] inclusion complex have similar binding affinity of -8.9 kcal/mol, indicating that the LE does not form specific interactions with the symmetric HPγCD. The top 1 docking structure of [LE@HPγCD] inclusion complex is as shown in FIG. 2. In the structure of [LE@HPγCD] inclusion complex, the polar moiety of LE is located outside the secondary face of HPγCD as well as the hydrophobic moiety is located inside the cavity of HPγCD.

TABLE 11

The top 5 docking results of [LE@HPγCD] inclusion complex.

| Mode | Affinity (kcal/mol) |
|---|---|
| 1 | -8.9 |
| 2 | -8.9 |
| 3 | -8.9 |
| 4 | -8.9 |
| 5 | -8.4 |

Figure 3:
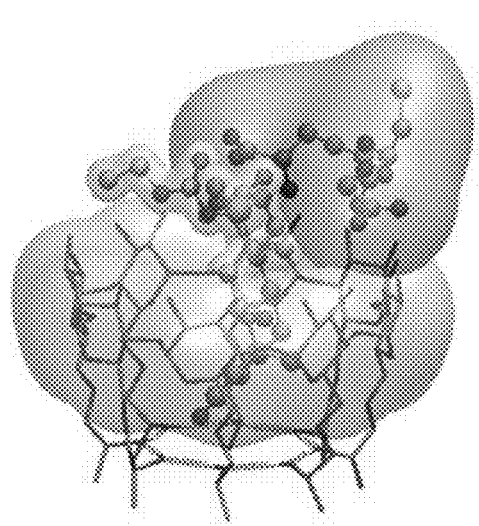
FIG. 3 shows the most stable structure of GSH-[LE@HPγCD] inclusion complex obtained from molecular docking analysis. (a) Side view; (b) Primary face view.
Figure 3:
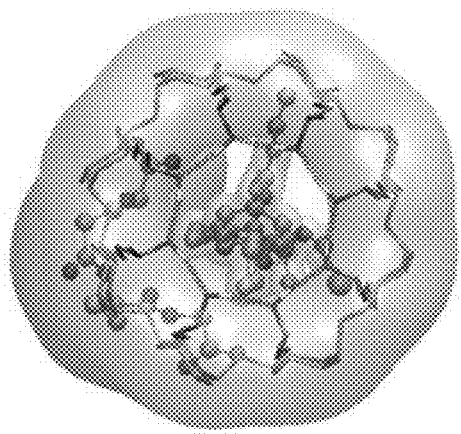

Table 12 lists the top 5 docking results of the GSH-[LE@HPγCD] inclusion complex. The GSH is located on the secondary face of HPγCD. The top 1 docking structure of GSH-[LE@HPγCD] inclusion complex is as shown in FIG. 3. In this structure, the GSH can prevent the LE to interact with water molecules directly.

TABLE 12

The top 5 docking results of GSH-[LE@HPγCD] inclusion complex.

| Mode | Affinity (kcal/mol) | GSH Location |
|---|---|---|
| 1 | -3.9 | Secondary Face |
| 2 | -3.8 | Secondary Face |
| 3 | -3.8 | Secondary Face |
| 4 | -3.7 | Secondary Face |
| 5 | -3.6 | Primary Face |

Figure 4:
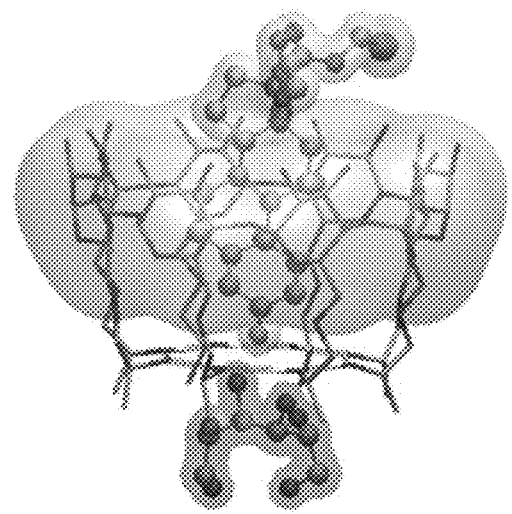
FIG. 4 shows the most stable structure of mannitol-[LE@HPγCD] inclusion complex obtained from molecular docking analysis.

Table 13 lists the top 5 docking results of mannitol-[LE@HPγCD] inclusion complex. The highly water-soluble mannitol served as a negative control is located on the primary face of HPγCD. The top 1 docking structure of mannitol-[LE@HPγCD] inclusion complex is as shown in FIG. 4. In this structure, the polar mannitol can form hydrogen-bonds with the hydroxypropyl groups of HPγCD, which might partially destroy the hydrogen-bond networks of hydroxypropyl groups.

TABLE 13

Top 5 docking results of mannitol-[LE@HPγCD] inclusion complex.

| Mode | Affinity (kcal/mol) |
|---|---|
| 1 | −3.4 |
| 2 | −3.3 |
| 3 | −3.3 |
| 4 | −3.3 |
| 5 | −3.2 |

Figure 5:
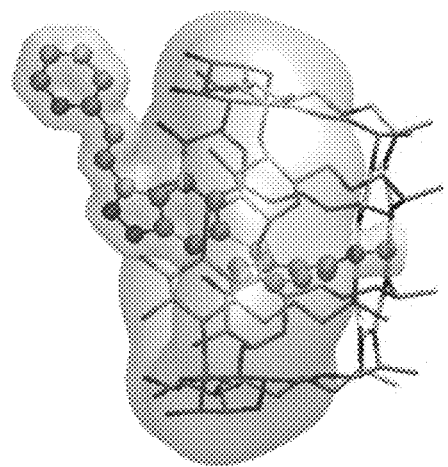
FIG. 5 shows the most stable structure of [axitinib@HPγCD] inclusion complex obtained from molecular docking analysis.

Table 14 lists the top 5 docking results of [axitinib@HPγCD] inclusion complex. The initial structures of axitinib and HPγCD used for docking simulations are obtained from DFT calculations mentioned above. It is observed that the top 5 docking results of [axitinib@HPγCD] inclusion complex have similar binding affinity of −8.6 kcal/mol, indicating that the axitinib does not form specific interactions with the symmetric HPγCD. The top 1 docking structure of [axitinib@HPγCD] inclusion complex is as shown in FIG. 5. In the structure of [axitinib@HPγCD] inclusion complex, the polar moiety of axitinib is located outside the primary face of HPγCD as well as the hydrophobic moiety is located inside the cavity of HPγCD.

TABLE 14

The top 5 docking results of [axitinib@HPγCD] inclusion complex.

| Mode | Affinity (kcal/mol) |
|---|---|
| 1 | −8.6 |
| 2 | −8.6 |
| 3 | −8.6 |
| 4 | −8.6 |
| 5 | −8.5 |

Figure 6:
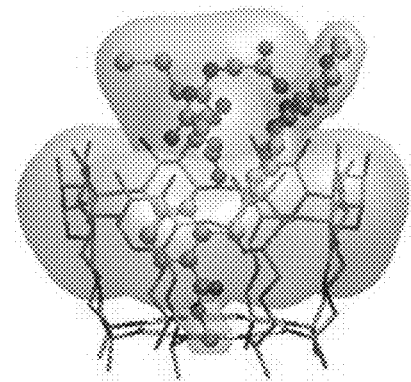
FIG. 6 shows the most stable structure of GSH-[axitinib@HPγCD] inclusion complex obtained from molecular docking analysis. (a) Side view; (b) Primary face view.
Figure 6:
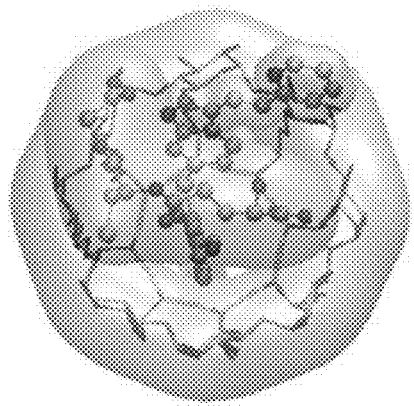

Table 15 lists the top 5 docking results of the GSH-[axitinib@HPγCD] inclusion complex. The GSH is located on the secondary face of HPγCD. The top 1 docking structure of GSH-[axitinib@HPγCD] inclusion complex is as shown in FIG. 6. In this structure, the stabilizer (GSH) can prevent the axitinib to interact with water molecules directly.

TABLE 15

Top 5 docking results of GSH-[axitinib@HPγCD] inclusion complex

| Mode | Affinity (kcal/mol) | GSH Location |
|---|---|---|
| 1 | −4.9 | Secondary Face |
| 2 | −4.8 | Secondary Face |
| 3 | −4.8 | Secondary Face |
| 4 | −4.6 | Secondary Face |
| 5 | −2.6 | Primary Face |

Figure 7:
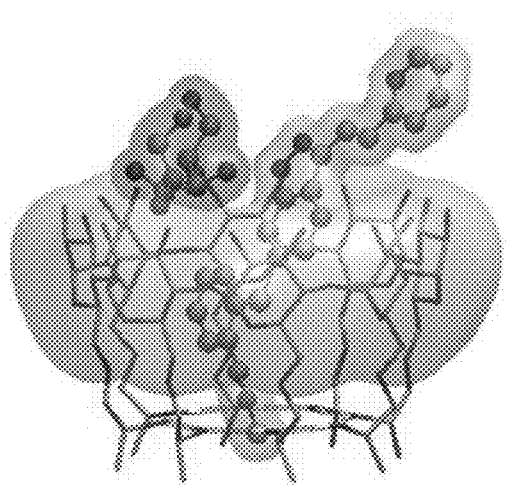
FIG. 7 shows the most stable structure of mannitol-[axitinib@HPγCD] inclusion complex obtained from molecular docking analysis. (a) Side view; (b) Primary face view.
Figure 7:
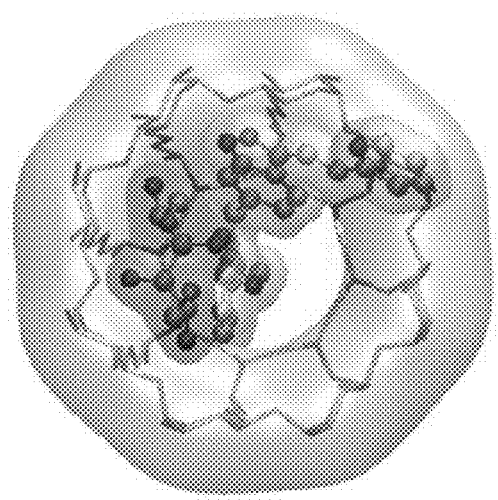

Table 16 lists the top 5 docking results of mannitol-[axitinib@HPγCD] inclusion complex. The mannitol is located on the secondary face of HPγCD. The top 1 docking structure of mannitol-[axitinib@HPγCD] inclusion complex is as shown in FIG. 7.

TABLE 16

Top 5 docking results of mannitol-[axitinib@HPγCD] inclusion complex.

| Mode | Affinity (kcal/mol) |
|---|---|
| 1 | −3.5 |
| 2 | −3.1 |
| 3 | −3.1 |
| 4 | −3.1 |
| 5 | −3.0 |

Figure 8:
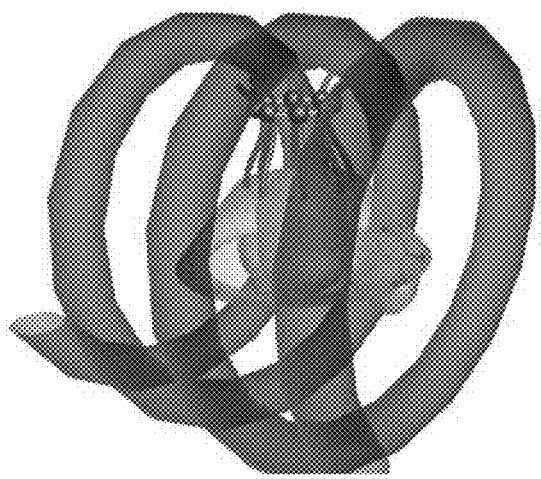
FIG. 8 shows the possible structures of HPMC[GSH-[LE@HPγCD]] and HPMC[GSH-[axitinib@HPγCD]] complex. (a) Hydroxypropyl methyl cellulose-GSH-[LE@HPγCD]; (b) hydroxypropyl methyl cellulose-GSH-[axitinib@HPγCD]
Figure 8:
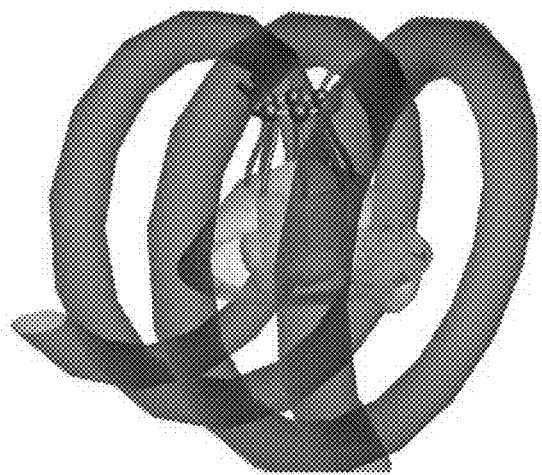
Figure 8:
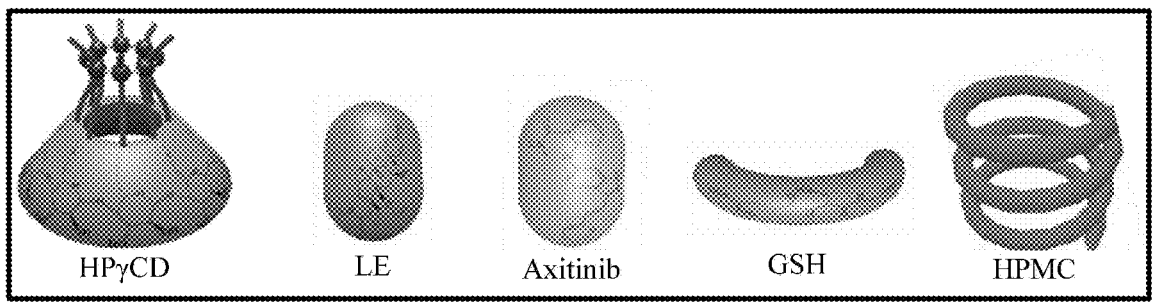

FIG. 8 illustrates the possible structures of hydroxypropyl methylcellulose GSH-[LE@HPγCD] and hydroxypropyl methylcellulose GSH-[axitinib@HPγCD] conjugates. The entanglement of HPMC with the inclusion complex can stabilize the [drug@HPγCD] inclusion complex.

3. Binding Energy of Inclusion Complexes

The binding energies of complexes were calculated with the basis set superposition error (BSSE) correction. The top 1 structure of complex from the docking calculations is used as the initial structure for further geometry optimization by B3LYP/6-31G(d) method. The vibrational frequencies of optimized complexes are further calculated to examine whether it is a stationary point or not. After all positive vibrational frequencies are obtained for the optimized complexes, the binding energy (ΔE) of complex is calculated by the following formula:

$$\Delta E = E_{complex} - (E_{ligand} + E_{HP\gamma CD})$$

Table 17 lists the binding energy of complexes. The smaller binding energy (−5.78 kcal/mol) of [drug@HPγCD] complex will allow the drugs to be released easily for performing its activity when the complex arrived at the target. Interestingly, the GSH has larger binding energy than mannitol. The rich H-bond donors and acceptors of mannitol make the mannitol highly water soluble (1.19 mol/L at 25° C.). The water solubility of GSH at 25° C. is 0.95 mol/L only.

Figures 9A, 9B:
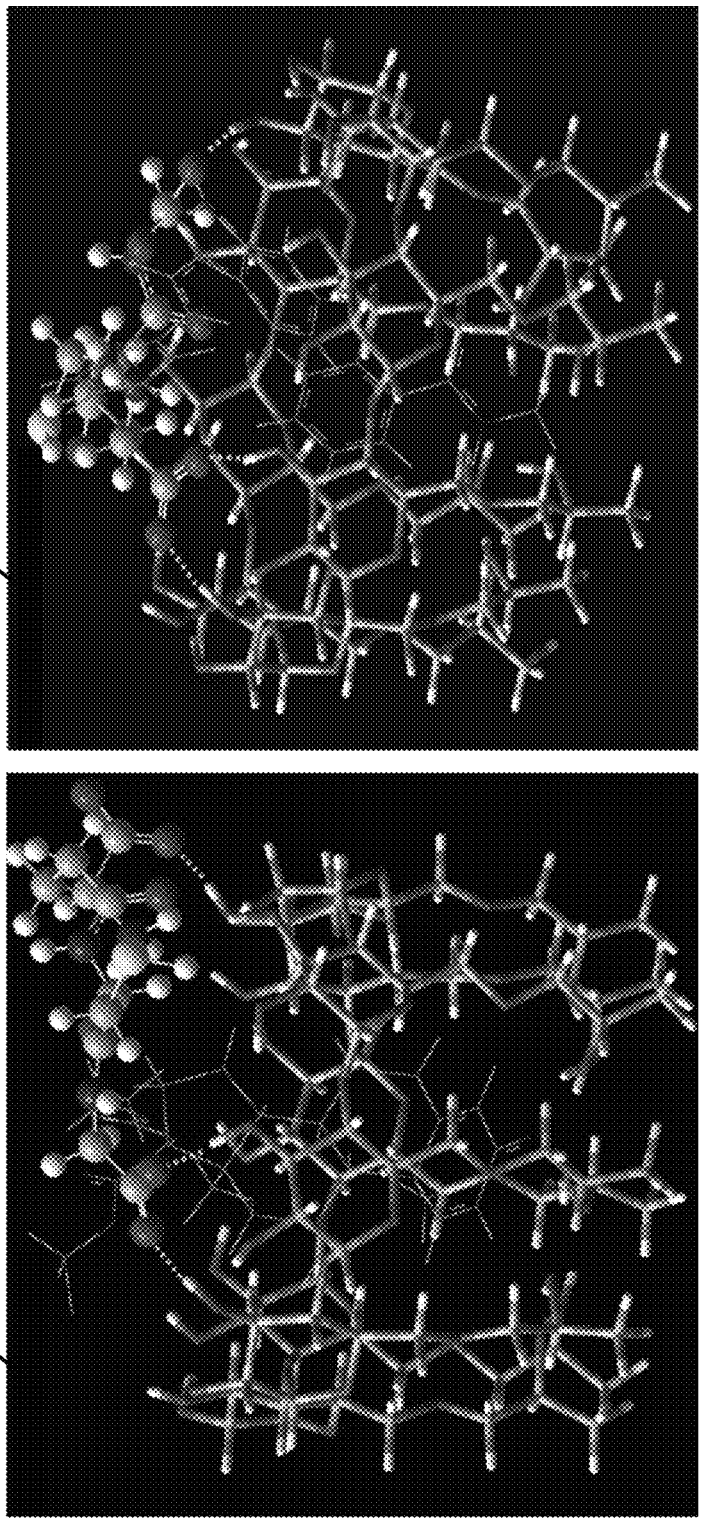
FIG. 9A shows the 3D structure of GSH4LE@HPγCD] inclusion complex.
FIG. 9B shows the 3D structure of GSH-[axitinib@HPγCD] inclusion complex.

Table 18 lists the relative energies (calculated at B3LYP/6-31G(d) level) of GSH-[axitinb@HPγCD] structures with the GHS located at the primary and secondary faces, respectively. Based on Table 18, it can be known that the GSH-[axitinb@HPγCD] structure with the GHS located at the secondary face is 9 kcal/mol more stable than the one with the GHS located at the primary face. FIGS. 9A and 9B respectively shows the 3D structures of GSH-[LE@HPγCD] and GSH-[axitinib@HPγCD] inclusion complexes highlighting the H-bond interactions between the GSH and the secondary face of HPγCD.

TABLE 17

The binding energies (kcal/mol) of inclusion complexes calculated at B3LYP/6-31G(d) level

| System 1 | LE vs HPγCD | GSH vs [LE@HPγCD] | Mannitol vs [LE@HPγCD] |
|---|---|---|---|
| Binding Energy (BSSE correction) | −5.97 | −74.37 | −40.64 |

TABLE 17-continued

The binding energies (kcal/mol) of inclusion complexes calculated at B3LYP/6-31G(d) level

| System 2 | axitinb vs HPγCD | GSH vs [axitinb@HPγCD] | Mannitol vs [axitinb@HPγCD] |
|---|---|---|---|
| Binding Energy (BSSE correction) | −8.91 | −76.31 | −29.67 |

TABLE 18

The relative energies (kcal/mol) of GSH-[axitinb@HPγCD] structures with GSH located at the primary and secondary faces calculated at B3LYP/6-31G(d) level.

| | Secondary Face | Primary Face |
|---|---|---|
| Relative Energy | 0.00 | 9.01 |

Example 4

Animal Experiment

Example 4-1

Determination of the Exposure Amount of Loteprednol Etabonate (LE)
1. Sample Preparation
The samples were prepared according to the formula shown in the following Table 19 at room temperature. The sample preparation method is analogous to the foregoing Example 1-4. In the Sample 2 of this example, Tween 80 was further added to aggregate the sample to form microparticles, and the formed microparticles have an average particle diameter of about 500 nm to 100 μm.

TABLE 19

| Number | Sample | LE (mg) | HPγCD (mg) | Caffeine (mg) | HPMC (mg) | Tween 80 (mg) | LE content (μg/mL) |
|---|---|---|---|---|---|---|---|
| 1 | HPC8C15LH | 2 | 204 | 15 | 10 | — | 1710.0 |
| 2 | HPC8C15LH-TW80 | 2 | 204 | 15 | 10 | 10 | 1686.6 |

—: No addition

2. Method for Determining Exposure Amount

Male New Zealand White rabbits with a body weight of about 2-3 kg were weighed and recorded before the experiment. The rabbit was placed in a Baoding rack. After the rabbit was in a stable state, the lower eyelids were opened to expose the conjunctival sacs. Then, a 35 μL eyedrop formula was taken by a pipetman and dropped into the conjunctival sacs of the right and left eyes of the white rabbit, separately. After that, the eyelids were closed and gently rubbed so that the eye drops can moisten the entire surface of the eyes.

At 0.5, 1, and 3 hours after administration, the white rabbits were sacrificed with $CO_2$. Next, the left and right eyeballs were washed with PBS solution, first, and then the left and right eyeballs were taken out. After taking out the left and right eyeballs, the taken eyeballs of the white rabbits were washed again with PBS solution, and the excess PBS solution was removed with a dust-free paper.

A 25 G syringe was used to puncture the posterior cornea to draw the aqueous humor (AH) out, and the aqueous humor was then placed in a 1.5 mL centrifuge tube. Next, the eyeball tissue and the centrifuge tube containing the aqueous humor were placed in liquid nitrogen for about 2 minutes to be rapidly frozen, and then stored in a −80° C. refrigerator for subsequent analysis for a drug content of a sample. 20 μL of aqueous humor sample or the standard for the drug with different concentrations was respectively added to a 1.5 mL centrifuge tube. 180 μL of ACN (acetonitrile) containing 0.1% TFA (Trifluoroacetic acid) was added to each centrifuge tube and mixed well. The centrifuge tube was placed in a centrifuge and centrifuged at 15,000 rpm for 10 minutes. The centrifuged sample was subjected to liquid chromatography-tandem mass spectrometry (LC-MS/MS) for quantitative analysis of drug concentration in the aqueous humor sample (LLOQ: 0.1 ng/mL), and the pharmacokinetic parameters were calculated (time required for reaching the highest blood drug concentration $T_{max}$, the highest blood drug concentration $C_{max}$, the area under blood drug concentration-time curve, AUC (Area under curve), etc.) to evaluate the ability of increasing corneal penetration of the formulations of the drug.

3. Results 2-1 Detemination of the Exposure Amount of Loteprednol Etabonate (LE)

The formulation of the present disclosure, HPC8C15LH, HPC8C15LH-TW80, or Lotemax (a commercial product of loteprednol etabonate (LE)) (Bausch & Lomb, Inc.) was respectively administered to the white rabbits by the aforementioned determination methods, and the results are as shown in the following Table 20.

TABLE 20

| PK parameter | $T_{max}$ (hour) | $C_{max}$ (ng/mL) | $AUC_{0-3\ hour}$ (hour × ng/mL) |
|---|---|---|---|
| Aqueous humor | | | |
| HPC8C15LH | 0.5 | 14.3 ± 1.8 | 17.7 ± 1.7 |
| HPC8C15LH-TW80 | 0.5 | 157.8 ± 37.2 | 145.3 ± 25.8 |
| Lotemax | 0.5 | 6 ± 1 | 14 ± 2 |
| Iris/Ciliary body | | | |
| HPC8C15LH | 0.5 | 471 ± 86 | 493 ± 43 |
| HPC8C15LH-TW80 | 0.5 | 95 ± 26 | 105 ± 23 |
| Lotemax | 0.5 | 49 ± 6 | 91 ± 5 |

According to Table 20, it can be known that the formulation of the present disclosure can enhance the penetration ability of the drug into the anterior chamber of the eye, and can increase the AUC of the drug in the aqueous humor by more than 10 times.

Example 4-2

Determination of the Exposure Amount of Axitinib
1. Sample Preparation

Samples were prepared according to the formulations as shown in Table 21 below at room temperature. The sample preparation method is analogous to the foregoing Example 2.

TABLE 21

| Number | Sample | Axitinib (mg) | HPγCD (mg) | Caffeine (mg) | HPMC (mg) | Benzalkonium chloride) (mg) | EDTA (mg) | Poloxamer 407 (mg) | Axitinib content (μg/mL) |
|---|---|---|---|---|---|---|---|---|---|
| 1 | HC8A solution | 6 | 408 | 30 | 5 | — | — | — | 3524.4 |

2. Method for Determining the Exposure Amount of the Drug

Figure 10:
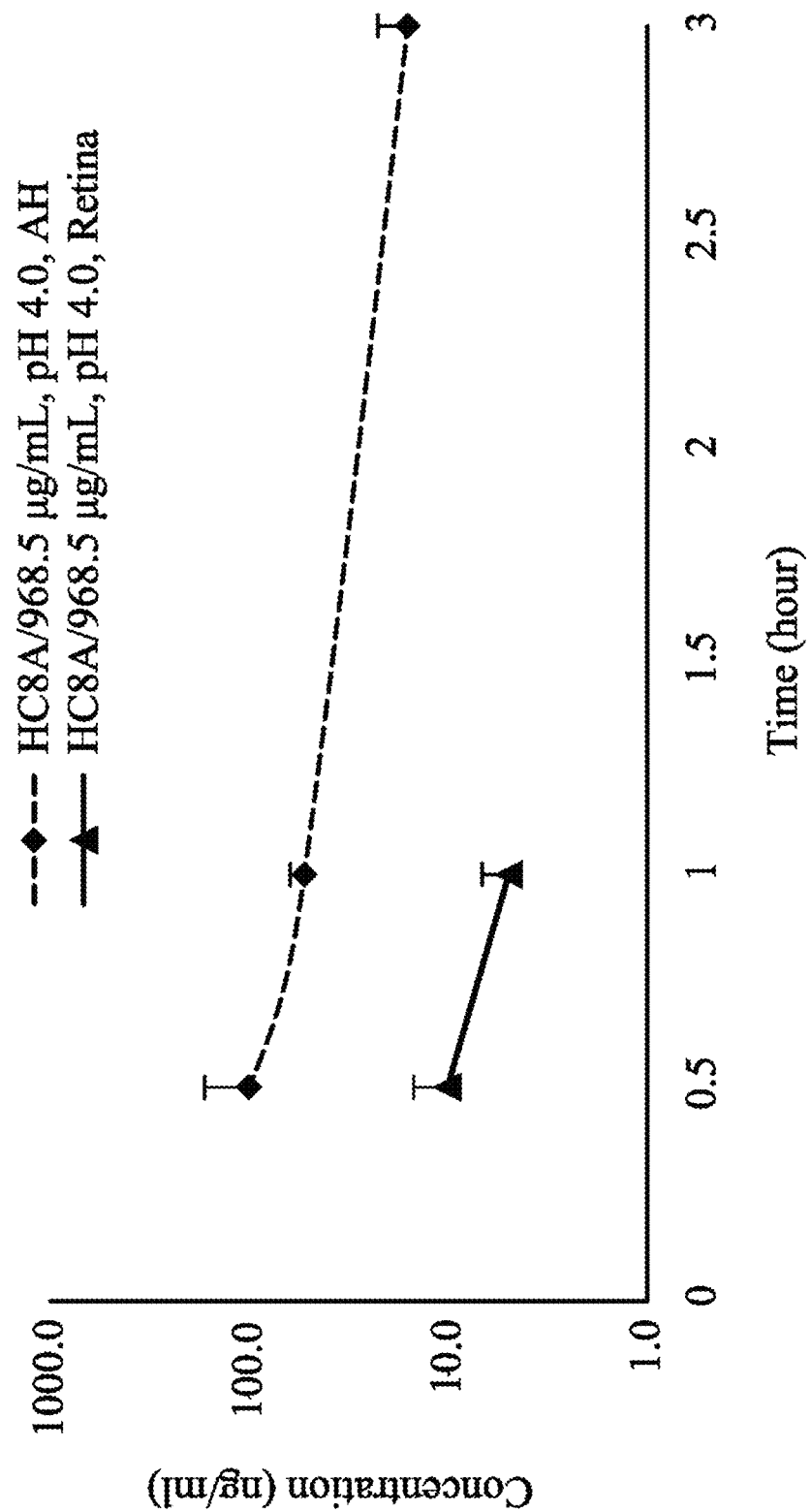
FIG. 10 shows the results of a pharmacokinetic test of HC8A solution for aqueous humor (AH) and retina of rabbit eyes in one embodiment of the present disclosure.

The formulation of HC8A solution of the present disclosure or axitinib-MPP (mucus penetrating particle (MMP) (Kala pharmaceuticals) was respectively administered to the white rabbits according to the method for determining the exposure amount of the drug described in the foregoing Example 4-1, and the results are as shown in Table 22 and FIG. 10.

TABLE 22

| PK parameter | $T_{max}$ (Hour) | $C_{max}$ (ng/mL) | $AUC_{0-3\ hour}$ (Hour × ng/mL) |
|---|---|---|---|
| Aqueous humor | | | |
| HC8A solution, 0.35% (axitinib concentration: 3.5 mg/mL) | 0.6 ± 0.3 | 244 ± 58 | 377 ± 62 |
| Retina | | | |
| HC8A solution, 0.35% | 0.5 | 58 ± 10 | 81 ± 22 |
| Axitinib-MPP 2% (axitinib concentration: 20 mg/mL) | 0.5 | 8.39 ± 2.16 | 78.1 ± 5.8 (0-24 hour) |

According to Table 22 and FIG. 10, it can be known that the formulation of the present disclosure can effectively deliver the drug to the posterior chamber, and thus can be effectively applied to the treatment of retro ocular diseases or lesions, such as macular degeneration.

Example 4-3

Adjuvant Induced Chronic Uveitis Model (AIU Model)
1. Sample Preparation

Samples were prepared according to the formulation as shown in Table 20 below at room temperature. The sample preparation method is analogous to the foregoing Example 1-2. In the sample of this example, Tween 80 is further added to aggregate the sample to form microparticles, and the formed microparticles have an average particle diameter of about 500 nm to 100 μm.

TABLE 23

| Number | Sample | LE (mg) | HPγCD (mg) | His (mg) | HPMC (mg) | Tween 80 (mg) | LE content (μg/mL) |
|---|---|---|---|---|---|---|---|
| 1 | HPC8H80LH/TW-PD | 2 | 204 | 80 | 10 | 10 | 1716.8 |

2. Experimental Method

Experimental animals: New Zealand White (NZW) rabbits, male, 2-2.5 kg.

Before the start of the experiment, the experimental animals were randomly grouped based on body weight to make each group have similar average body weight and body weight distribution trend.

Figure 11:
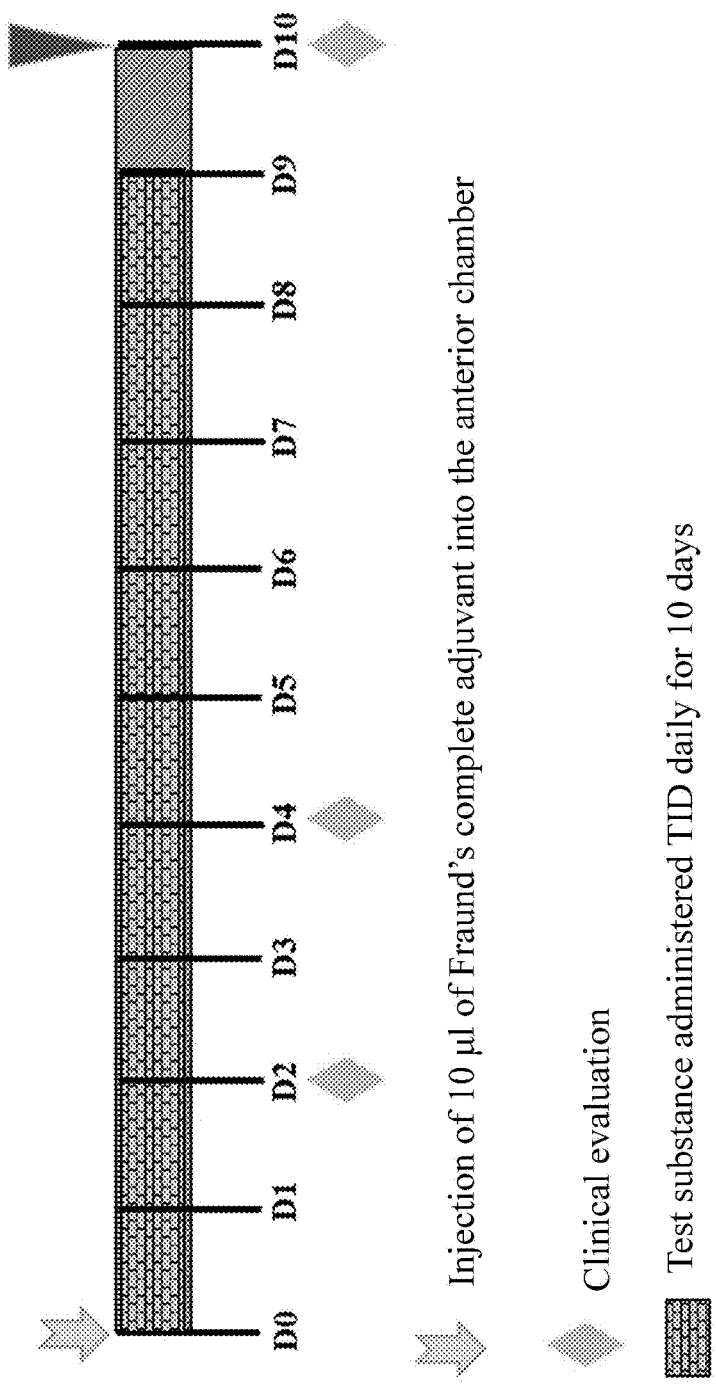
FIG. 11 shows the time course of an experiment of an adjuvant induced chronic uveitis model (AIU model) according to one embodiment of the present disclosure.
Figure 12:
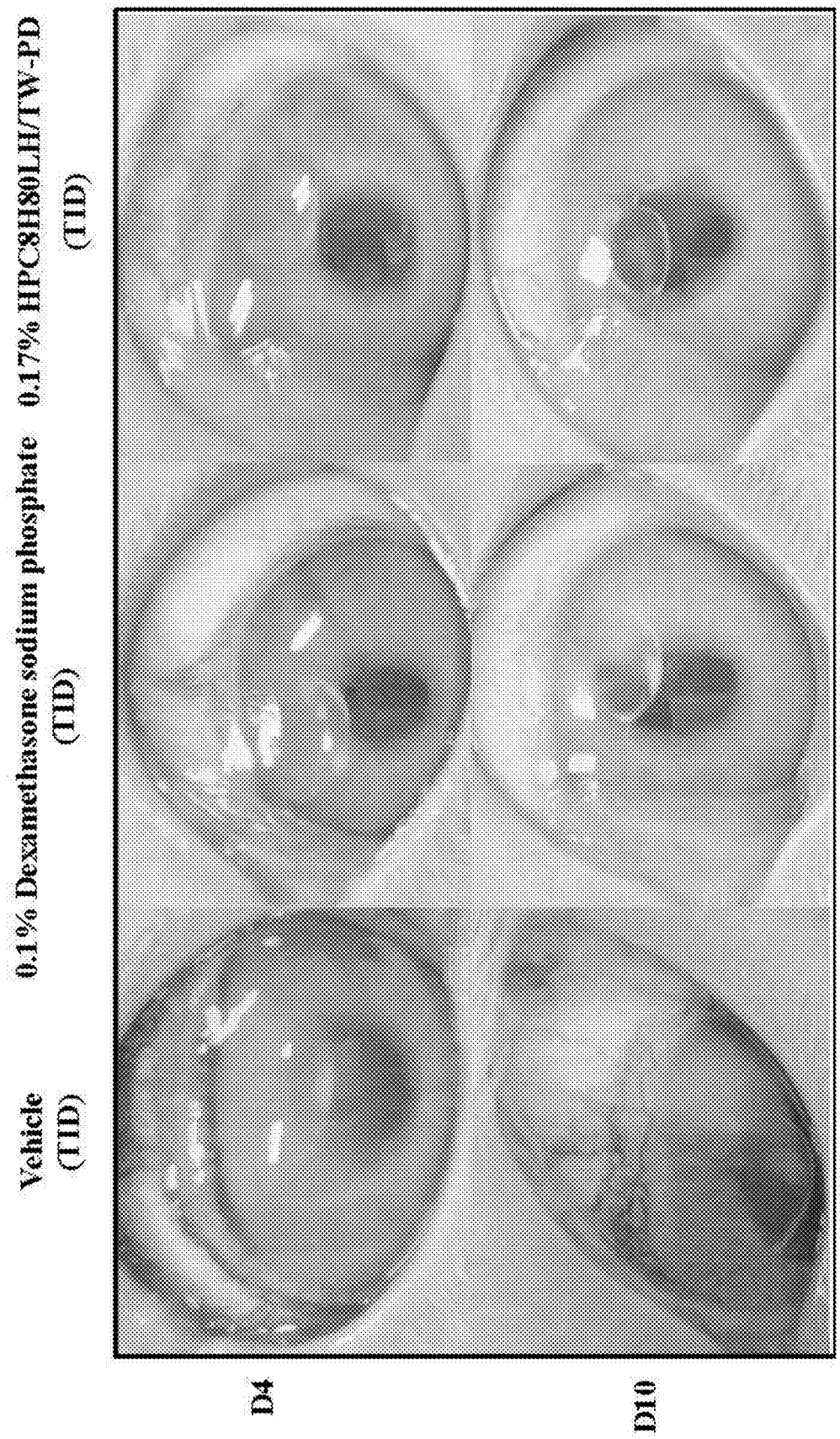
FIG. 12 shows the photographs of eyes of the rabbit photographed on Day 4 and Day 10 in an experiment of an adjuvant induced chronic uveitis model according to one embodiment of the present disclosure in which a vehicle, 0.1% dexamethasone sodium phosphate and the composition of the present disclosure (0.17% HPC8H80LH/TW-PD) was respectively administered to the eyes of the rabbits at a frequency of three times a day (TID)
Figure 13A:
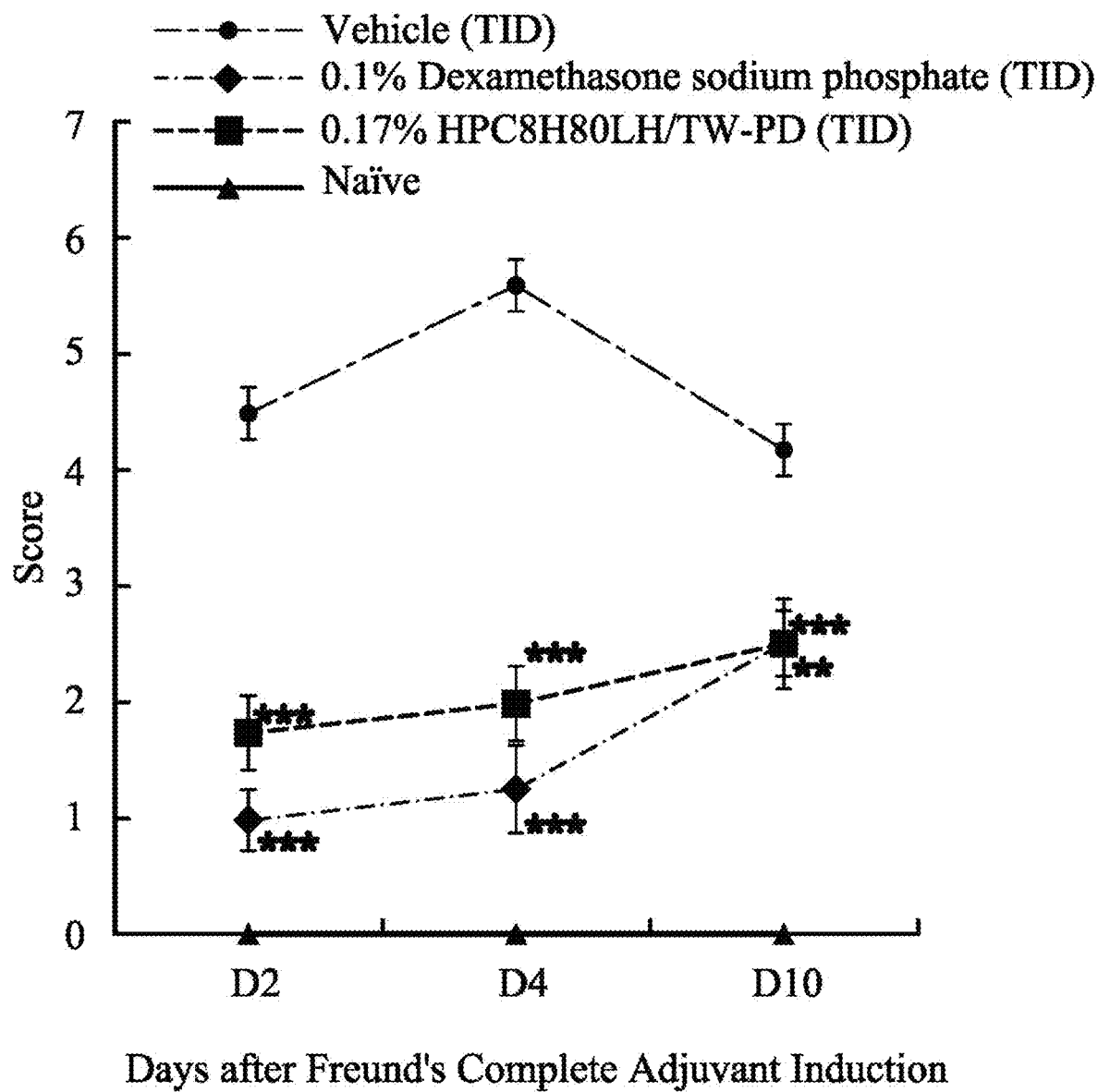
FIG. 13A shows the scoring results for the conjunctival congestion degree in the rabbit eyes of the vehicle treated group, the 0.1% dexamethasone sodium phosphate treated group, the composition of the present disclosure (0.17% HPC8H80LH/TW-PD) treated group and untreated group in an experiment of an adjuvant induced chronic uveitis model according to one embodiment of the present disclosure.
Figure 13B:
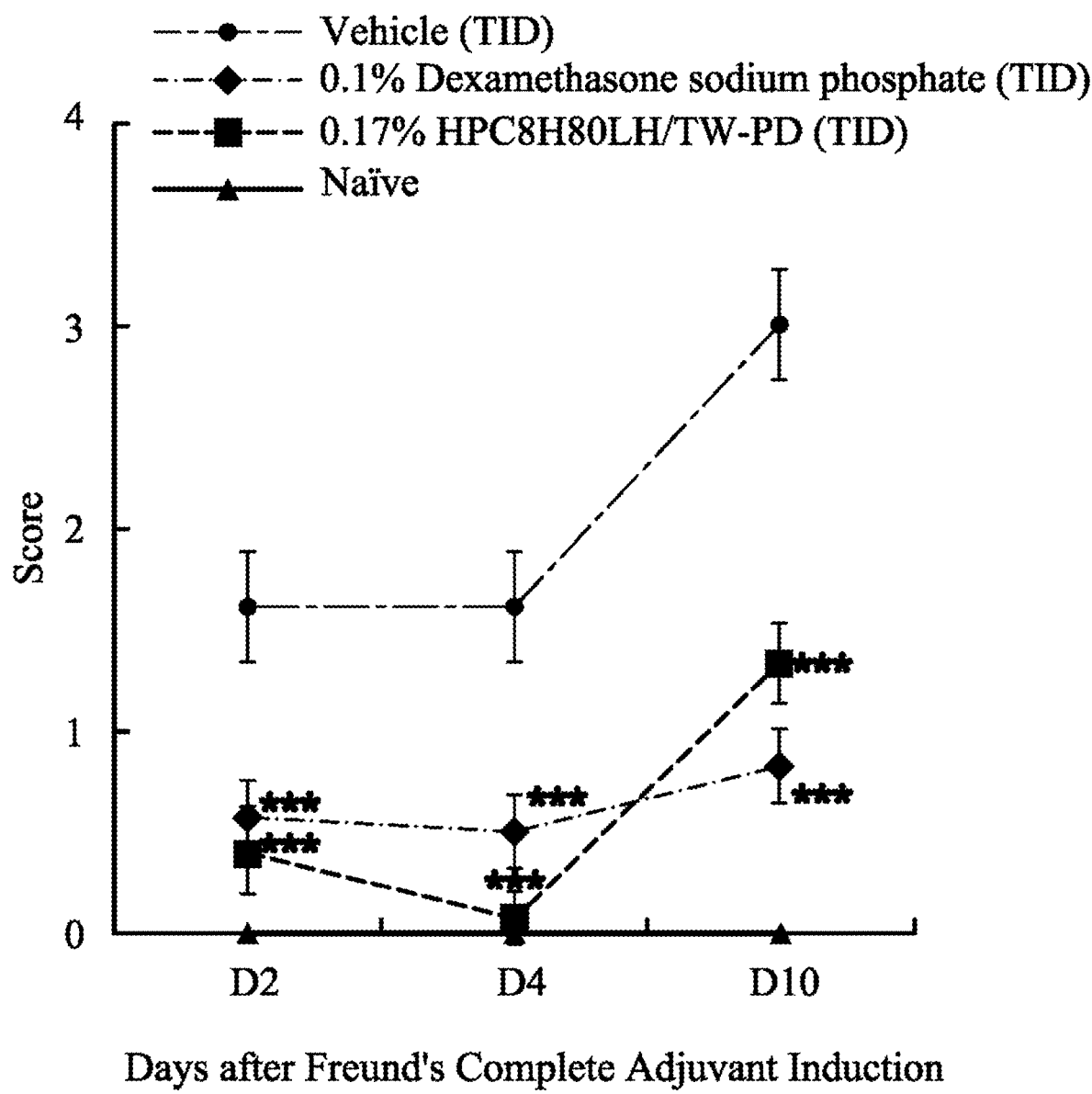
FIG. 13B shows the scoring results for anterior chamber flare degree in the rabbit eyes of the vehicle treated group, the 0.1% dexamethasone sodium phosphate treated group, the composition of the present disclosure (0.17% HPC8H80LH/TW-PD) treated group and untreated group in an experiment of an adjuvant induced chronic uveitis model according to one embodiment of the present disclosure.
Figure 13C:
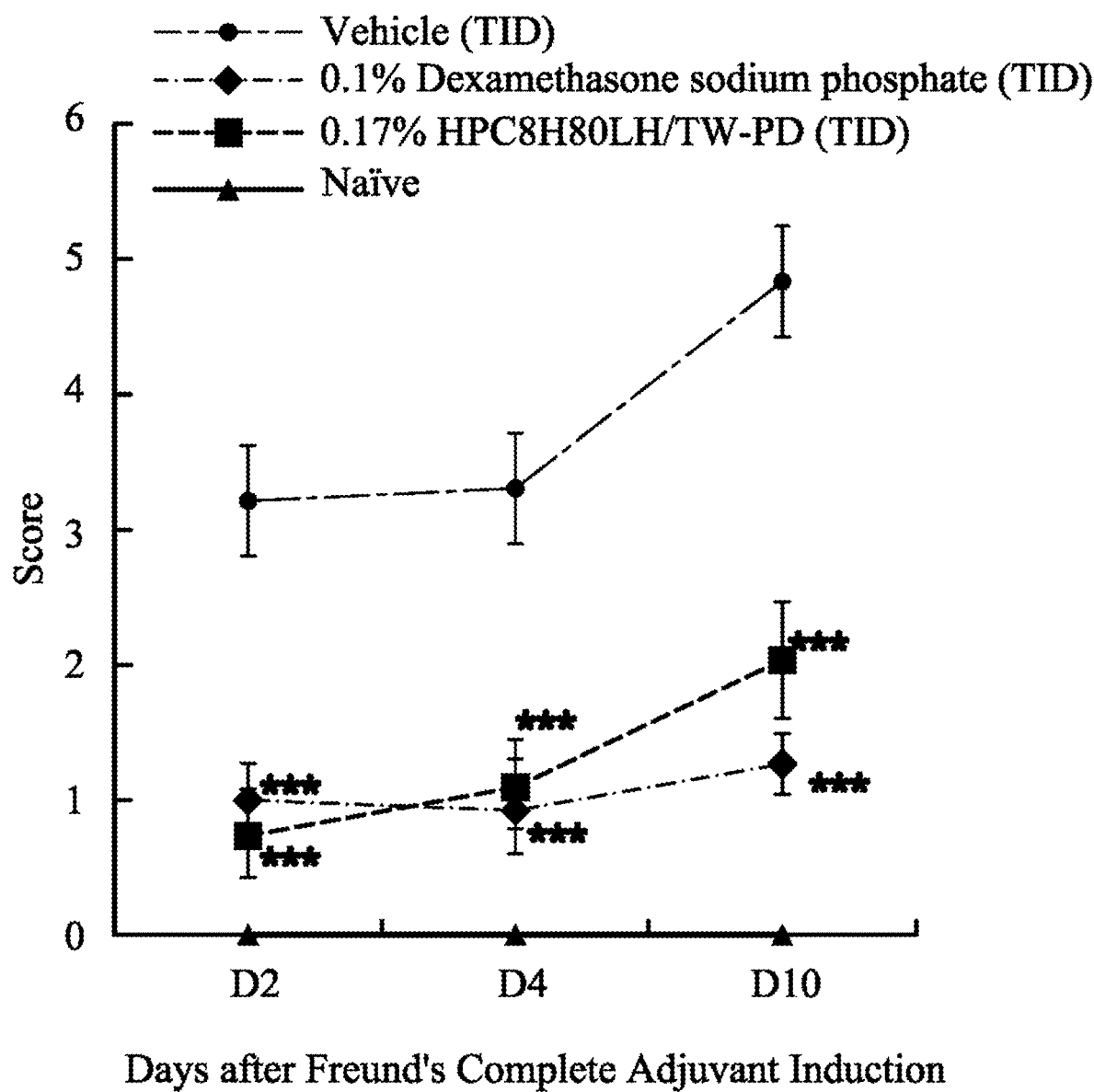
FIG. 13C shows the scoring results for uveitis condition in the rabbit eyes of the vehicle treated group, the 0.1% dexamethasone sodium phosphate treated group, the composition of the present disclosure (0.17% HPC8H80LH/TW-PD) treated group and untreated group in an experiment of an adjuvant induced chronic uveitis model according to one embodiment of the present disclosure.

An adjuvant induced chronic uveitis model test was performed according to the time course as shown in FIG. 11.

On Day 0 (D0), the experimental animals were anesthetized with an anesthetic (Zoletil 50: 40 mg/kg+xylazine: 10 mg/kg) through intramuscular injection (IM), and then 10 μl Freund's Complete Adjuvant (CFA) was administered to both eyeballs through anterior chamber injection by a 30 G micro syringe.

Thereafter, the test drug was administered on Day 0 (D0). The test substance was administered to both eyes in the form of eye drops, three times a day, each time in a volume of 35 μL/eye, and administered continuously for 10 days.

On Day 2 (D2), Day 4 (D4), and Day 10 (D10), both eyes of the experimental animals were observed with a slit lamp, and the degree of conjunctival congestion, the degree of anterior chamber flare and the condition of uveitis were respectively scored or graded according to the standards of grading as shown in Tables 24, 25, and 26 below to assess the state of intraocular inflammation.

Thereafter, the experimental animals were sacrificed with an excess of $CO_2$ gas on Day 10 (D10), and the aqueous humor was taken for analyses for infiltration count of inflammatory cell, protein production, and PGE2 production.

TABLE 24

| Scoring for conjunctival congestion degree | |
|---|---|
| Score | Condition |
| 0 | Normal |
| 1 | Mild dilation |
| 2 | Moderate siltation |
| 3 | Diffuse redness |

Bellot JL et al., 1996

TABLE 25

Scoring for anterior chamber flare degree

| Grade | Condition |
|---|---|
| 0 | None |
| 1 | Faint |
| 2 | Moderate (iris and lens details clear) |
| 3 | Marked (iris and lens details hazy) |
| 4 | Intense (fibrin or plastic aqueous) |

THE STANDARDIZATION OF UVEITIS NOMENCLATURE (SUN) WORKING GROUP, 2005

TABLE 26

Scoring for uveitis condition

| Clinical signs | Grade of uveitis (score) |
|---|---|
| Iris hyperemia | |
| Absent | 0 |
| Mild | 1 |
| Moderate | 2 |
| Severe | 3 |
| Pupil | |
| Normal | 0 |
| Miosed | 1 |
| Exudate in anterior chamber | |
| Absent | 0 |
| Small | 1 |
| Large | 2 |
| Hypopyon | |
| Absent | 0 |
| Present | 1 |
| Maximum possible score | 7 |

Hoekzema R et al., 1991

3. Results

The rabbits were separately administered with vehicle, 0.1% dexamethasone sodium phosphate, and 0.17% HPC8H80LH/TW-PD (loteprednol etabonate concentration: 1.7 mg/mL) according to the method described above. The results are as shown in FIG. 12 and FIGS. 13A to 13C.

According to FIG. 12 and FIGS. 13A to 13C, it can be known that the formulation of the present disclosure can effectively improve conjunctival congestion, anterior chamber flare and uveitis.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A composition for improving the solubility of poorly soluble substances, comprising:
    40-99.5% by weight of cyclodextrin and/or a derivative thereof;
    0.05-10% by weight of at least one water-soluble polymer; and
    0.05-20% by weight of at least one water-soluble stabilizer, wherein the at least one water-soluble stabilizer comprises adenine or guanine.

2. The composition for improving the solubility of poorly soluble substances as claimed in claim 1, wherein the cyclodextrin comprises α-cyclodextrin, β-cyclodextrin, γ-cyclodextrin, δ-cyclodextrin or a combination thereof.

3. The composition for improving the solubility of poorly soluble substances as claimed in claim 1, wherein the derivative of cyclodextrin comprises hydroxypropyl modified cyclodextrin, succinyl modified cyclodextrin, methyl modified cyclodextrin or a combination thereof.

4. The composition for improving the solubility of poorly soluble substances as claimed in claim 3, wherein the hydroxypropyl modified cyclodextrin comprises hydroxypropyl-γ-cyclodextrin (hydroxypropyl-γ-CD).

5. The composition for improving the solubility of poorly soluble substances as claimed in claim 1, wherein the at least one water-soluble polymer comprises hydroxypropyl methyl cellulose (HPMC), hydroxypropyl cellulose, carboxymethyl cellulose (CMC), polyvinylpyrrolidone, (PVP), polyvinyl alcohol, poly(ethylene glycol)-poly(propylene glycol)-poly (ethylene glycol) (PEG-PPG-PEG (ABA)) triblock copolymer or a combination thereof.

* * * * *